US010954307B2

(12) United States Patent
Kahil et al.

(10) Patent No.: US 10,954,307 B2
(45) Date of Patent: Mar. 23, 2021

(54) TARGETED DELIVERY METHODS AND COMPOSITIONS FOR ANTIHISTAMINES

(71) Applicant: LIPIDAIR, LLC, Houston, TX (US)

(72) Inventors: Michael Dale Kahil, Houston, TX (US); Tawanda Gumbo, Southlake, TX (US)

(73) Assignee: LIPIDAIR, LLC, Houston, TX (US)

( * ) Notice: Subject to any disclaimer, the term of this patent is extended or adjusted under 35 U.S.C. 154(b) by 0 days.

(21) Appl. No.: 15/852,766

(22) Filed: Dec. 22, 2017

(65) Prior Publication Data

US 2018/0179297 A1 Jun. 28, 2018

Related U.S. Application Data

(60) Provisional application No. 62/438,101, filed on Dec. 22, 2016.

(51) Int. Cl.

| | |
|---|---|
| ***C07K 16/00*** | (2006.01) |
| ***A61K 39/395*** | (2006.01) |
| ***C07K 16/42*** | (2006.01) |
| ***A61K 9/127*** | (2006.01) |
| ***A61P 37/08*** | (2006.01) |
| ***A61K 9/00*** | (2006.01) |
| ***A61K 31/4545*** | (2006.01) |
| ***A61K 31/4418*** | (2006.01) |
| ***A61K 31/5513*** | (2006.01) |
| ***C07K 16/28*** | (2006.01) |
| ***A61K 47/69*** | (2017.01) |
| ***A61K 31/4402*** | (2006.01) |
| ***A61K 31/445*** | (2006.01) |
| ***A61K 31/55*** | (2006.01) |
| ***A61K 31/495*** | (2006.01) |
| ***A61K 47/68*** | (2017.01) |
| ***A61K 31/451*** | (2006.01) |
| ***A61K 31/40*** | (2006.01) |

(52) U.S. Cl.

CPC ........ *C07K 16/4291* (2013.01); *A61K 9/0073* (2013.01); *A61K 9/127* (2013.01); *A61K 31/40* (2013.01); *A61K 31/4402* (2013.01); *A61K 31/445* (2013.01); *A61K 31/4418* (2013.01); *A61K 31/451* (2013.01); *A61K 31/4545* (2013.01); *A61K 31/495* (2013.01); *A61K 31/55* (2013.01); *A61K 31/5513* (2013.01); *A61K 47/6849* (2017.08); *A61K 47/6913* (2017.08); *A61P 37/08* (2018.01); *C07K 16/283* (2013.01); *C07K 2317/76* (2013.01); *C07K 2317/92* (2013.01)

(58) Field of Classification Search

CPC ............ A61K 31/4545; A61K 31/4418; A61K 31/5513; A61K 47/6913; A61K 31/4402; A61K 31/445; A61K 31/55; A61K 31/495; A61K 47/6849; A61K 31/451; A61K 31/40; A61K 9/127; C07K 16/283; C07K 2317/76; C07K 2317/92; C07K 16/4291

See application file for complete search history.

(56) References Cited

U.S. PATENT DOCUMENTS

| | | | | |
|---|---|---|---|---|
| 2005/0170451 | A1* | 8/2005 | Sugimura ............ | C07K 16/283 435/69.1 |
| 2005/0202077 | A1 | 9/2005 | Watson et al. | |
| 2007/0128298 | A1* | 6/2007 | Cowley ................ | A61K 31/135 424/722 |
| 2009/0220583 | A1* | 9/2009 | Pereswetoff-Morath .................... | A61K 9/127 424/450 |
| 2013/0171137 | A1* | 7/2013 | Mitre ................. | A61K 39/3955 424/133.1 |
| 2014/0065203 | A1 | 3/2014 | Pereswetoff-Morath et al. | |
| 2014/0314783 | A1* | 10/2014 | Finkelman ......... | A61K 39/3955 424/143.1 |

(Continued)

FOREIGN PATENT DOCUMENTS

| | | |
|---|---|---|
| WO | 01/39799 | 6/2001 |
| WO | 0139799 A2 | 6/2001 |

(Continued)

OTHER PUBLICATIONS

M Salim, H Minamikawa, A Sugimura, R Hashim. "Amphiphilic designer nano-carriers for controlled release: from drug delivery to diagnostics." Medicinal Chemistry Communications, vol. 5, 2014, pp. 1602-1618. Published on Sep. 2, 2014. (Year: 2014).*

(Continued)

*Primary Examiner* — Mark Halvorson
(74) *Attorney, Agent, or Firm* — McGurk Group LLC

(57) ABSTRACT

Products, compositions, and methods for using one or more small particles to facilitate the delivery of one or more antihistamines to a human body are disclosed. In some aspects, methods are disclosed that utilize small particles that may be integrated with one or more guiding antibodies that detect and bind to high affinity immunoglobulin E receptors associated with various types of target cells, such as mast cells, basophils, and dendritic cells. Methods in accordance with the present disclosure may use small particles that are configured to contain relatively high concentrations of at least one form of at least one antihistamine and deliver the antihistamine(s) to areas within a human body where one or more actions associated with an allergic reaction may be in progress and/or where one or more actions associated with an allergic reaction may be likely to occur.

28 Claims, 14 Drawing Sheets

Specification includes a Sequence Listing.

(56) References Cited

U.S. PATENT DOCUMENTS

2014/0322246 A1 10/2014 Karagiannis et al.

FOREIGN PATENT DOCUMENTS

| | | | |
|---|---|---|---|
| WO | 2010/051056 | | 5/2010 |
| WO | 2010051056 | A2 | 5/2010 |
| WO | 2010/127108 | | 11/2010 |
| WO | 2010127108 | A2 | 11/2010 |
| WO | 2012/169741 | | 12/2012 |
| WO | 2012169741 | A2 | 12/2012 |
| WO | 2013066179 | A1 | 5/2013 |

OTHER PUBLICATIONS

Y Fan, Q Zhang. "Development of liposomal formulations: From concept to clinical investigations." Asian Journal of Pharmaceutical Sciences, vol. 8, 2013, pp. 81-87. (Year: 2013).*

P Ramos-Cabrer, F Campos. "Liposomes and nanotechnology in drug development: focus on neurological targets." International Journal of Nanomedicine, vol. 8, 2013, pp. 951-960. (Year: 2013).*

MV Khodoun, ZY Kucuk, RT Strait, D Krishnamurthy, K Janek, CD Clay, SC Morris, FD Finkelman. "Rapid desensitization of mice with anti-FcgRIIb/FcgRIII mAb safely prevents IgG-mediated anaphylaxis." Journal of Allergy and Clinical Immunology, vol. 132 No. 6, 2013, pp. 1375-1387. (Year: 2013).*

MV Khodoun, ZY Kucuk, RT Strait, D Krishnamurthy, K Janek, I Lewkowich, SC Morris, FD Finkelman. "Rapid polyclonal desensitization with antibodies to IgE and FcϵRIa." Journal of Allergy and Clinical Immunology, vol. 131 No. 6, 2013, pp. 1555-1564e.7 (17 total sheets). (Year: 2013).*

United States Patent and Trademark Office .RW Bahr. "Clarification of Written Description Guidance for Claims Drawn to Antibodies and Status of 2008 Training Materials." Memorandum on Feb. 22, 2018. 2 printed pages. (Year: 2018).*

US Patent and Trademark Office. "Antibody Decisions and Their Compliance with the Written Description Requirement." Obtained from https://www.uspto.gov/sites/default/files/documents/Antibody_1172015.pptx on Jul. 5, 2018, originally published 2015, pp. 1-27. (Year: 2015).*

R Kontermann, U Brinkmann. "Bispecific Antibodies." Drug Discovery Today, vol. 20 No. 7, Jul. 2015, pp. 838-847. (Year: 2015).*

Invitrogen. "FceR1 alpha Monoclonal Antibody (MAR-1), eBioscience™." https://www.thermofisher.com/order/genome-database/generatePdf?productName=FceR1%20alpha&assayType=PRANT&detailed=true&productId=14-5898-81 accessed Oct. 29, 2018, 6 printed pages. (Year: 2018).*

MP Alphonse, AS Saffar, L Shan, KT HayGlass, FER Simons, AS Gounni. "Regulation of the High Affinity IgE Receptor (FceRI) in Human Neutrophils: Role of Seasonal Allergen Exposure and Th-2 Cytokines." PLoS ONE, vol. 3 Issue 4, e1921, Apr. 2008, pp. 1-8. (Year: 2008).*

United States Court of Appeals for the Federal Circuit. *Amgen* v. *Sanofi*. Case 2017-1480. Decided Oct. 5, 2017, pp. 1-24. (Year: 2017).*

United States Court of Appeals for the Federal Circuit. *Abbvie* v. *Janssen*. Case 2013-1338,-1346. Decided Jul. 1, 2014, pp. 1-38. (Year: 2014).*

International Search Report and Written Opinion, International Patent Application No. PCT/US2017/068237, dated Mar. 19, 2018.

Khodoun et al., "Rapid polyclonal desensitization with antibodies to IgE and FcϵRIα," J Allergy Clin Immunol. Jun. 2013;131(6):1555-64. doi: 10.1016/j.jaci.2013.02.043. Epub Apr. 28, 2013.

Zheng, "Pharmacokinetic and Pharmacodynamic Evaluation of the Relationship Between Peripheral H1-Receptor Blockade with Serum and Skin Concentrations of H1-Receptor Antagonists Hydroxyzine and Cetirizine after Oral Administration in Humans and Evaluation of the Distribution and Efficacy of Hydroxyzine and Cetirizine in Solution and Liposome Formulations Applies Topically to Rabbits," Thesis to the Faculty of University of Manitoba. 1995, 1-148.

Yi Zheng, "Pharmacokinetic and Pharmacodynamic Evaluation of the Relationship Between Peripheral H1 Receptor Blockade with Serum and Skin Concentrations of H1 Receptor Antagonists Hydroxyzine and Cetirizine After Oral Administration in Humans and . . . "; Thesis submitted to the Faculty of Graduate Studies of the Univ. of Manitoba, Master of Science, copyright 1995.

PCT Preliminary Report on Patentability, dated Jul. 4, 2019.

* cited by examiner

SEQUENCE LISTING

```
<160> NUMBER OF SEQ ID NOS: 10

<210> SEQ ID NO 1
<211> LENGTH: 349
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

gaggtgcagc tgcaggagtc tggacctgag ctggtgaagc ctggggcttc ggtgaagata     60

tcctgtaagg cttctggata cacgttcact gactactaca tgaactgggt gaagcagagc    120

catggaaaga gccttgagtg gattggatat attaatccta acaatgatga tactagctac    180

aaccagaagt tcaagggcaa ggccacattg actgtagaca agtcctccag cacagcctac    240

atggagctcc gcagcctaac atctgaggac tccacagtct attactgtgc aagatgggac    300

tggtacttcg atgtctgggg cacagggacc acggtcaccg tctcctcat               349


<210> SEQ ID NO 2
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Val Gln Leu Gln Glu Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Tyr Ile Asn Pro Asn Asn Asp Asp Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Thr Val Tyr Tyr Cys
                85                  90                  95

Ala Arg Trp Asp Trp Tyr Phe Asp Val Trp Gly Thr Gly Thr Thr Val
```

```
            100                 105                 110

Thr Val Ser Ser
        115


<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Tyr Thr Phe Thr Asp Tyr Tyr
1               5


<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ile Asn Pro Asn Asn Asp Asp Thr
1               5


<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Arg Trp Asp Trp Tyr Phe Asp Val
1               5


<210> SEQ ID NO 6
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

gacattgtga tgacccagtc tcaaaaattc atgtccacaa cagtaggaga cagggtcagc      60

atcacctgca agggcagtca gaaagtggct actgctgtag cctggtatca acagaaacca     120

ggacaatctc ctaaactact gatttactca gcatccaatc ggtatattgg agtccctgat     180

cgcttcacag gcagtggatc tgggacagac ttcactctca ccattagcaa tatgcagtct     240

gaagacctgg catattattt ctgtcaacaa tatagcagtc atccgtggac gttcggtgga     300

ggcaccaagc tggaaatcaa ac                                              322


<210> SEQ ID NO 7
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
```

-continued

```
<400> SEQUENCE: 7

Asp Ile Val Met Thr Gln Ser Gln Lys Phe Met Ser Thr Thr Val Gly
1               5                   10                  15

Asp Arg Val Ser Ile Thr Cys Lys Gly Ser Gln Lys Val Ala Thr Ala
            20                  25                  30

Val Ala Trp Tyr Gln Gln Lys Pro Gly Gln Ser Pro Lys Leu Leu Ile
        35                  40                  45

Tyr Ser Ala Ser Asn Arg Tyr Ile Gly Val Pro Asp Arg Phe Thr Gly
    50                  55                  60

Ser Gly Ser Gly Thr Asp Phe Thr Leu Thr Ile Ser Asn Met Gln Ser
65                  70                  75                  80

Glu Asp Leu Ala Tyr Tyr Phe Cys Gln Gln Tyr Ser Ser His Pro Trp
                85                  90                  95

Thr Phe Gly Gly Gly Thr Lys Leu Glu Ile Lys
            100                 105


<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Lys Val Ala Thr Ala
1               5


<210> SEQ ID NO 9
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ser Ala Ser
1


<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln Gln Tyr Ser Ser His Pro Trp Thr
1               5
```

TARGETED DELIVERY METHODS AND COMPOSITIONS FOR ANTIHISTAMINES

RELATED APPLICATIONS

This application claims the benefit under 35 U.S.C. § 119(e) to U.S. Provisional Application No. 62/438,101, filed on Dec. 22, 2016, which is hereby incorporated herein by reference in its entirety.

SEQUENCE LISTING

The instant application contains a Sequence Listing which has been submitted electronically in ASCII format and is hereby incorporated by reference in its entirety. Said ASCII copy, created on Oct. 19, 2020, is named LipidairSL.txt and is 5,626 bytes in size.

FIELD OF THE DISCLOSURE

The present disclosure generally relates to compositions and methods for treating allergic reactions within the human body and more particularly to compositions and methods that utilize one or more small particles to deliver one or more antihistamines to various locations within a given human body and/or otherwise intervene in one or more actions associated with an allergic reaction occurring within the body.

BACKGROUND

The statements in this section merely provide background information related to the present disclosure.

Antihistamines are often used to counter the effects caused by the histamine molecules released during an allergic reaction. However, antihistamines cause side effects when used to treat an allergic reaction. For example, H1 antagonists, one type of antihistamine, are transported across the blood-brain barrier and thereby cause unwanted side effects to the central nervous system, including drowsiness, confusion, blurred vision, difficulty sleeping, nightmares, hallucinations, difficulty emptying the bladder, and constipation.

Antihistamines are typically delivered orally by pills, tablets, capsules, or liquid; or intravenously especially during emergencies. None of these forms of delivery are ideal because oral antihistamines take a considerable amount of time before taking effect (such as, for example, up to two hours), while intravenous delivery requires painful needles that pose safety concerns and require specific medical expertise that patients may not possess.

SUMMARY

This Summary is provided to preliminarily introduce concepts that are further described below in the Detailed Description section.

Small particles, such as nanoparticles, have been developed to deliver antihistamines to certain parts and/or regions of the human body. The payload of the delivery can be increased to increase the concentration of antihistamine by using nanoparticles. However, several issues remain to be addressed in the delivery of antihistamines. Nanoparticles are beneficial in that (i) they have the ability to increase the concentration of drugs delivered to the body or parts of the body by increasing the payload of the delivery mechanism, (ii) by their controlled release rates of the drugs with the effect of increasing the biological half-life or to extend the duration of their release into the bloodstream, (iii) by protecting different organs from potential side-effect damage associated with various drugs by shielding the entry and release of one or more drugs from one or more specific locations, and (iv) by target release of these molecules to certain parts of the body where their effects are desired by targeting one or more specific cells within the body.

Nanoparticles can be designed to include various degrees of target cell specificity based on the desired location of drug effect within a human body and/or what types of interactions they will cause within the body. This specificity is typically achieved by designing nanoparticles such that they are drawn to one or more particular receptors associated with one or more intended target cells. This is often accomplished by developing one or more antibodies that are on the surfaces of nanoparticles and are designed to bind to specific receptors on specific cells. One of the properties of antibodies is the high specificity they have for particular receptors. The antibodies may be configured upon the surfaces of the nanoparticles in order to cause the nanoparticles to essentially seek out and bind to the intended receptors, thereby allowing them to release relatively high concentrations of one or more drugs to targeted cells without causing damage to other parts of the body.

Additionally, special antibodies called blocking antibodies are configured to bind to a target (such as a receptor on a cell or an antigen), but instead of producing the effect(s) normally associated with binding to the receptor, they inhibit such effect(s). Blocking antibodies prevent other antibodies and/or antigens from binding to the target and thereby prohibit the effects that would otherwise occur when such other antibodies/antigens are bound to the target. For example, blocking antibodies can be designed to deter ligation effects that would normally occur when certain receptors are occupied. In fact, blocking antibodies have been developed for clinical use, particularly with regard to cancer treatment where they block the functions of certain proteins to alter the functioning of various immune system cells to enhance their effectiveness against cancer cells.

Additionally, antihistamines have the potential to produce a variety of negative side effects within the human body, particularly when they are delivered to the entire body systemically in relatively high concentrations, as is often the case with oral administration and/or when multiple forms of antihistamines are delivered simultaneously. Of particular concern are side effects that impact the central nervous system. Furthermore, one class of antihistamines—corticosteroids—also creates an increased risk of infection because they are immunosuppressing agents.

To address these issues, a method for delivering one or more small particles, including nanoparticles such as liposomes, that contain one or more antihistamines to a human body are provided. Also provided are one or more new small particles configured to facilitate rapid delivery of the antihistamine(s) to specified/targeted locations within the body. Methods for making and delivering one or more small particles that contain one or more antihistamines to the human body while minimizing the side effects associated with the antihistamine(s) are also provided. Additionally, methods for making and delivering one or more small particles that contain one or more antihistamines to the body that allow maximum concentrations of one or more antihistamines to be administered to the body are provided. Furthermore, methods for making and delivering small particles to the body that are capable of carrying and delivering more than one form of one or more antihistamines simultaneously that work to prevent different steps of an allergy cascade are also provided.

Aspects of the present disclosure provide methods for making and delivering small particles which facilitate the delivery of one or more antihistamines to a human body. Specifically, in one aspect, methods are disclosed that utilize various types of small particles that are configured to carry one or more antihistamines and quickly deliver them to one or more locations within a human body, including certain regions, systems, organs, and/or cells. The types of small particles may take on various forms, including nanoparticles, such as liposomes, and may be introduced into the body via numerous ways, including via inhalation. In some aspects, each small particle may comprise one or more antihistamines in significantly large quantities and/or concentrations in order to maximize the effectiveness of treatment of one or more actions associated with one or more allergic reactions.

Methods of the present disclosure may utilize guiding antibodies associated with the small particles that may comprise a bifunctional utility in that in addition to the guiding function, they may also provide one or more blocking functions by being configured to prevent the occurrence of one or more actions associated with an allergic reaction within the human body. Methods using such small particles may begin, for example, when one or more small particles are received by the human body via a human respiratory system, using the nose or intravenously.

In some aspects, methods in accordance with the present disclosure may utilize one or more small particles that are integrated with one or more bifunctional antibodies. Such bifunctional antibodies may perform guiding functions to target cells (specifically mast cells and basophils), blocking antibody functions, or both guiding and blocking functions. The guiding functions may allow the small particles to transport and deliver the antihistamine(s) to one or more specific locations, regions, processes, functions, diseases, disorders, systems, organs, and/or cells within a human body. Methods that include such targeted delivery negate the need to deliver high concentrations of an antihistamine to the entire body and/or away from sites associated with an allergy cascade, thereby minimizing potential side effects. Such methods also allow multiple antihistamines to be delivered to the body simultaneously as the possibility of them interacting negatively with each other in a way that is detrimental to the body is minimized. Additionally, the guiding functions of the bifunctional antibodies may serve to keep the small particles with which they are associated (and also the antihistamine(s) within them) away from the body's blood-brain barrier in order to minimize and/or prevent side effects associated with the central nervous system.

In other aspects wherein targeted delivery of one or more antihistamines may be desired for the methods associated with the present disclosure, such targeted delivery may be achieved when the guiding functions of the bifunctional antibodies associated with the small particles cause the small particles to specifically find and bind to FcεRI receptors associated with certain target cells, such as mast cells and/or basophils. When the small particles are taken to such targeted cells, they are able to deliver the antihistamine(s) in relatively large quantities and/or concentrations, and thereby prevent as well as intervene in an ongoing allergy cascade.

Additionally, methods in accordance with the present disclosure may use small particles that are integrated with bifunctional antibodies that may include blocking functions. These blocking functions may allow the bifunctional antibodies to occupy FcεRI receptors associated with target cells in order to prevent IgE antibodies from binding to them. When the bifunctional antibodies occupy the FcεRI receptors, no cross-linking reaction takes place, thereby preventing the allergy cascade that would otherwise occur if the FcεRI receptors were occupied by IgE antibodies bound to allergens. The word bifunctional is used herein to denote that the antibodies may lead to two types of effects, and not necessarily to denote that the antibodies need to bind to two different antigens. Indeed, the antibodies may bring about the two effects by binding to FcεRI (which, even without the duplicative word "receptor" following it, denotes the high-affinity IgE receptor).

In some aspects, the small particles used with the methods in accordance with the present disclosure may take the form of nanoparticles. In some additional aspects, such nanoparticles may comprise liposomes. In still some additional aspects, the small particles may comprise at least two generally concentric lipid spheres separated by at least one dividing layer, thereby allowing them to contain at least two different forms of antihistamines, with one form of antihistamine contained within each sphere. Any antihistamine(s) contained within the small particles may be released via a variety of processes, such as, for example, where one or more outer surfaces and/or membranes of the small particles are broken down or by a specified controlled release rate out of each layer.

In some aspects, at least two different variations of small particles may be used with methods in accordance with the present disclosure. These different variations may be delivered to an individual simultaneously or separately. Such different variations of small particles may comprise different sizes and/or configurations. Small particles of different variations may be designed to travel to various different locations within a human body and/or change the time and/or duration of release of one or more antihistamines that they carry within the body.

Aspects of an embodiment involve (1) binding of monoclonal antibodies to the FcεR on basophils and mast cells; (2) that the binding does not produce cross-linking and therefore degranulation (that is the antibodies are blocking antibodies); and (3) that they are used as guiding antibodies to deliver one or more anti-histamines in nanoparticles. Since these are antibodies of the FcεR, and do not bind to IgE (i.e, they are not anti-IgE) they avoid the problem of triggering the allergy cascade that is a problem of monoclonal anti-IgE antibodies. IgE itself forms a very stable interaction with FcεRI which has a very slow dissociation rate, and thus mast cells and basophils of patients display allergen specific IgE on surfaces with a half-life of 10 days (i.e., "practically permanently"), so that when next time they encounter the allergen there is rapid release of the mediators by these cells. Each basophil from patients with allergic reactions for example may have $10^4$ to $10^6$ FcεRI receptors. The monoclonal antibody that is on the market, omalizumab, neutralizes free IgE (which it binds with a $k_D$ of $1.5\times10^{-8}$ M) but does not interfere with FcεRI-bound IgE; a different mechanism from the antibodies disclosed here. In other words, embodiments of the compositions disclosed here do not change the IgE; instead, they are specifically targeted at the receptor that IgE binds.

In one aspect, the disclosure provides a drug delivery compound (DDC) targeted to an FcεRI, in which the DDC includes a nanoparticle, an antihistamine, and at least one anti-FcεRI antibody. In an embodiment, the antihistamine is within the nanoparticle, and the antibody is attached to the nanoparticle. FcεRI is a receptor, specifically the high-affinity IgE receptor. The antibodies, in an embodiment, are monoclonal antibodies. The antibodies can also be Fab fragments, single-domain antibodies, single-chain variable fragments, or any other antibody variant that would bind to the FcεRI.

In an embodiment, the DCC contains more than one type of antihistamine (e.g., two, three, four, five, six). In various embodiments, the antihistamine can be mast cell stabilizers, basophil stabilizers. H1 antagonists, corticosteroids, leukotriene receptor antagonists, or combinations thereof. The nanoparticle, in some embodiments, is a liposome. In various embodiments, the DCC's have varying sizes (e.g., larger sizes to allow delivery to the respiratory system of a patient, and smaller sizes to allow delivery to the systemic circulation of a patient). In an embodiment, the DCC is in an aerosolized form.

In another aspect, the disclosure provides a composition having a nanoparticle, at least one antihistamine, and an antibody, in which the nanoparticle, the at least one antihistamine, and the antibody form a drug delivery compound (DDC) configured to bind to an FcεRI, and in which the at least one antihistamine is present at a low dose. Alternatively, the antihistamine may be present at a normal or high dose, in which case it would be used at a low dosage.

In an embodiment, the antihistamine can be a mast cell stabilizer, a basophil stabilizer, an H1 antagonist, a corticosteroid, or a leukotriene receptor antagonist. When more than one antihistamine is used, combinations of these types of antihistamines can be deployed. In an embodiment, the nanoparticle is a liposome. When multiple antihistamines are used, they may be distributed in different parts of the nanoparticle, for example, for a liposome, in an embodiment, one type of antihistamine is within an aqueous core of the liposome, and a second type of antihistamine is within a lipid bilayer of the liposome. In some embodiments, the composition further includes a second DCC, wherein the nanoparticles of the second DCC are smaller. In an embodiment, the composition is in an aerosolized from.

In an additional aspect, the disclosure provides a method for treating allergic reactions. The method includes forming or acquiring a drug delivery compound (DDC) that has a nanoparticle, an antihistamine, and an antibody; and delivering the DDC to an FcεRI in a patient.

In some embodiments, the method also includes delivering the antihistamine to a histamine receptor in the patient. In an embodiment, the DCC comprises a second antihistamine. In various embodiments, the method also includes binding of the antibody to the FcεRI to prevent or minimize both cross-linking of IgE and release of mediators. In an embodiment, the method includes aerosolizing the DCC before delivery to the patient. In some embodiments, the antihistamine can be chosen from any one of mast cell stabilizers, basophil stabilizers, H1 antagonists, corticosteroids, leukotriene receptor antagonists, and combinations thereof. In an embodiment, the nanoparticle is a liposome. In some embodiments, the FcεRI is on a target cell, which target cell can be a mast cell, a basophil, and a dendritic cell.

In an aspect, the disclosure provides a method for treating allergic reactions comprising forming or acquiring a composition comprising a nanoparticle, at least one antihistamine, and at least one antibody, wherein the nanoparticle, the antihistamine, and the antibody form a drug delivery compound (DDC) configured to bind to an FcεRI, and wherein the at least one antihistamine is present at a low dose.

In an embodiment, the method further includes administering the DDC to a patient. The method, in various embodiments, further includes delivering the at least one antihistamine to a histamine receptor in the patient. The method may further include binding of the antibody to the FcεRI to prevent or minimize cross-linking of IgE and release of mediators. In some embodiments, the DDC may be administered to the patient a second time after at least two days following the prior administration. The antihistamines can include mast cell stabilizers, basophil stabilizers, antagonists, corticosteroids, leukotriene receptor antagonists, and combinations thereof. The nanoparticle can be a liposome. The target cell with FcεRI can be a mast cell, a basophil, or a dendritic cell. In some embodiments, the method also includes delivery of the DCC to portions of a respiratory system of the patient. In some embodiments, the method, alternatively or additionally, also includes delivery of the DCC to portions of a systemic circulation of the patient.

In an aspect, the disclosure provides a composition that includes a nanoparticle having an FcεR targeting moiety extending from an external surface of the nanoparticle and an amount of an antihistamine contained within the nanoparticle.

In some embodiments, the composition further includes a second type of antihistamine within the nanoparticle. The antihistamine can be azelastine, carbinoxamine, cyproheptadine, desloratadine, emedastine, hydroxyzine, levocabastine, levocabastine, brompheniramine, cetirizine, chlorpheniramine, clemastine, diphenhydramine, fexofenadine, or loratadine. When multiple antihistamines are used, a combination of the foregoing can be used. The nanoparticle can be a liposome. The targeting moiety can be a peptide, a small molecule, or an antibody. The FcεR targeting moiety can be an FcεRI targeting moiety.

In another aspect, the disclosure provides a formulation that has a composition that includes a nanoparticle having an FcεR targeting moiety extending from an external surface of the nanoparticle and an amount of an antihistamine contained within the nanoparticle. Such a formulation is formulated for low-dose delivery of antihistamine.

The antihistamine, in some embodiments, can be azelastine, carbinoxamine, cyproheptadine, desloratadine, emedastine, hydroxy zinc, levocabastine, levocabastine, brompheniramine, cetirizine, chlorpheniramine, clemastine, diphenhydramine, fexofenadine, or loratadine. When multiple antihistamines are used, a combination of the foregoing can be used. The nanoparticle can be a liposome. When a liposome contains multiple antihistamines, such antihistamines may be in the aqueous core or the lipid bilayer of the liposome. In some embodiments, the formulation includes a second composition, which is configured for an extended release (e.g., by virtue of having nanoparticles with a different size than those of the other composition). The formulation may be formulated for aerosol delivery.

In an aspect, the disclosure provides a method for treating allergic reactions, in which the method includes obtaining a composition having a nanoparticle with an FcεR targeting moiety extending from an external surface of the nanoparticle, and an amount of an antihistamine contained within the nanoparticle; and delivering the composition to an FcεR in a patient.

In some embodiments, the method also includes delivering the antihistamine to a histamine receptor in the patient. The composition may include a second type of antihistamine within the nanoparticle. The targeting moiety may be a peptide, a small molecule, or an antibody. In one embodiment, the targeting moiety is a monoclonal antibody, the method further includes binding of the monoclonal antibody to the FcεR to prevent or minimize cross-linking of IgE and release of mediators. The antihistamine can be azelastine, carbinoxamine, cyproheptadine, desloratadine, emedastine, hydroxyzine, levocabastine, levocabastine, brompheniramine, cetirizine, chlorpheniramine, clemastine, diphenhydramine, fexofenadine, or loratadine. When multiple antihistamines are used, a combination of the foregoing can be used. The nanoparticle can be a liposome. The FcεR can be on a target cell such as a mast cell, a basophil, or a dendritic cell.

In another aspect, the disclosure provides a method for treating allergic reactions, the method including obtaining a formulation that has a composition, wherein the composition includes a nanoparticle having an FcεR targeting moiety extending from an external surface of the nanoparticle, and an amount of an antihistamine contained within the nanoparticle, wherein the formulation is formulated for low-dose delivery of antihistamine.

In an embodiment, the method further includes administering the formulation to a patient. The method may also include delivering the antihistamine to a histamine receptor in the patient. In an embodiment, the method includes administering the formulation to the patient a second time after at least two days following the prior administration. The antihistamine may be azelastine, carbinoxamine, cyproheptadine, desloratadine, emedastine, hydroxyzine, levocabastine, levocabastine, brompheniramine, cetirizine, chlorpheniramine, clemastine, diphenhydramine, fexofenadine, or loratadine. When multiple antihistamines are used, a combination of the foregoing can be used. The nanoparticle can be a liposome. In some embodiments, the method also includes binding of the antibody to an FcεRI on a target cell to prevent or minimize cross-linking of IgE and release of mediators. The target cell can be a mast cell, a basophil, or a dendritic cell. In some embodiments, the method includes delivery of the formulation to portions of a respiratory system of the patient. In some embodiments, alternatively or additionally, the method also includes delivery of the formulation to portions of a systemic circulation of the patient.

In various embodiments, the targeting moiety is a monoclonal antibody that has a dissociation constant selected from $8.15\times10^{-8}$, $4.21\times10^{8}$, $4.75\times10^{-8}$, $1.88\times10^{-7}$, and $8.53\times10^{-8}$ molar as measured by an Octet® RED96 instrument.

Further features and advantages of the present disclosure, as well as the structure and operation of various aspects of the present disclosure, are described in detail below with reference to the accompanying drawings.

BRIEF DESCRIPTION OF THE DRAWINGS

The features and advantages of the present disclosure will become more apparent from the Detailed Description set forth below when taken in conjunction with the drawings in which like reference numbers indicate identical or functionally similar elements.

DETAILED DESCRIPTION

Figure 1:
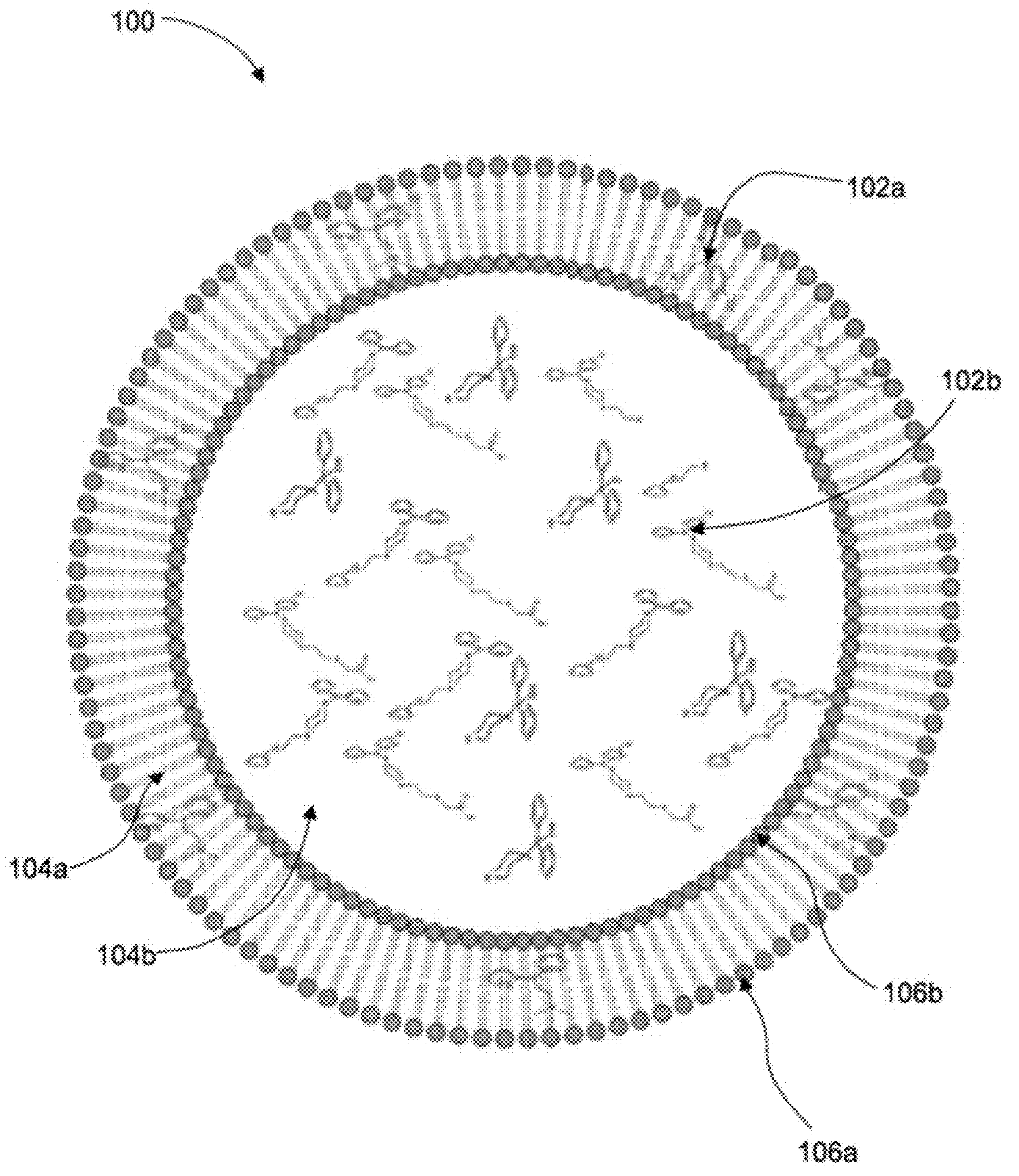
FIG. 1 is a cutaway view of an exemplary small particle for facilitating the delivery of one or more antihistamines to one or more locations within a human body, according to an aspect of the present disclosure.

The present disclosure is directed to compositions and methods that use one or more small particles to facilitate the delivery of one or more antihistamines to a human body. Aspects of the present disclosure provide methods that use one or more small particles to transport one or more antihistamines to one or more locations within a human body. In some aspects, methods are disclosed that utilize small particles that may be integrated with one or more bifunctional antibodies that serve to guide the small particles to one or more locations, regions, processes, functions, diseases, disorders, systems, organs, and/or cells within a human body and/or block one or more unwanted activities or actions from occurring at such sites. In some additional aspects, the small particles that are used with the disclosed methods may comprise nanoparticles, such as liposomes. In still some additional aspects, the one or more antihistamines contained within the small particles may comprise various types and/or forms.

The term "antihistamine" and/or the plural form of this term are used throughout herein to refer to any medicine or other substance that serves to intervene, prevent, treat, and/or alleviate one or more actions and/or symptoms associated with an allergic reaction or allergy cascade within a human body, such as mast cell stabilizers, basophil stabilizers, $H_1$ antagonists (including selective $H_1$ antagonists), corticosteroids, leukotriene receptor antagonists, and the like. Some examples of antihistamines that can be used include azelastine, carbinoxamine, cyproheptadine, desloratadine, emedastine, hydroxyzine, levocabastine, levocabastine, brompheniramine, cetirizine, chlorpheniramine, clemastine, diphenhydramine, fexofenadine, loratadine, and combinations thereof.

The term "small particle" and/or the plural form of this term are used throughout herein to refer to any molecule, cell, substance, structure, or container, either naturally occurring or manmade, capable of encompassing one or more antihistamines and delivering them to one or more locations within a human body, such as nanoparticles, liposomes, nanocrystals, polymeric micelles, protein-based nanoparticles, dendrimers, carbon nanotubes, polymer-drug conjugates, and the like. Such small particles may, in some aspects, be integrated with one or more guiding and/or blocking antibodies.

The term "delivery device" and/or the plural form of this term are used throughout herein to refer to any mechanism or apparatus capable of introducing one or more small particles and/or antibodies, including bifunctional antibodies, into a human body, such as electronic cigarettes, electronic vaporizers, jet nebulizers, ultrasome nebulizers, vibrating mesh nebulizers, metered dose inhalers, thy powder inhalers, nasal spray pumps, misting devices, vaporization devices, humidifiers, atomization devices, and the like.

The term "targeting moiety" is used to refer to a moiety that has an affinity to a particular target. For example, when attached to the nanoparticles, a targeting moiety increases the affinity of the nanoparticle-moiety composition toward the target, which can be an FcεR. In some embodiments, FcεR is FcεRI. The targeting moiety may be a peptide, small molecule, or an antibody. When the targeting moiety is an antibody, it can be a monoclonal antibody. Fab, scVc, and other antibody fragment that retains the ability to bind to a target antigen.

The term "extending from" is used to describe, in the context of a targeting moiety (e.g., mAb) extending from an external surface of a nanoparticle, that the targeting moiety has at least some of its portions outside of the nanoparticle. In other words, when a targeting moiety extends from the external surface of a nanoparticle, some of it may pass through the surface. Alternatively, when a targeting moiety extends from the external surface of a nanoparticle, the targeting moiety may be entirely on or outside of the nanoparticle (e.g., when it is connected via a linker to the nanoparticle).

Referring now to FIG. 1, a cutaway view of an exemplary small particle 100 for facilitating the delivery of one or more antihistamines 102 (labeled only as antihistamines 102*a-b* in FIG. 1, for clarity) to one or more locations within a human body, according to an aspect of the present disclosure, is shown.

In some aspects, small particle 100 may comprise a nanoparticle, such as a liposome. In some additional aspects, small particle 100 may be at least partially contained within one or more dry powder mixtures or liquid solutions and/or at least partially contained within one or more aqueous aerosol droplets. One or more of these droplets may be configured to be inhaled by a human respiratory system 400 (not shown in FIG. 1) with or without the assistance of one or more delivery devices.

Small particle 100 may be configured to encompass at least one form of one or more antihistamines 102. Antihistamine(s) 102 may comprise a variety of types and/or forms as will be appreciated by those skilled in the relevant art(s) after reading the description herein, including but not limited to mast cell stabilizers, basophil stabilizers, $H_1$ antagonists (including selective $H_1$ antagonists), corticosteroids, and leukotriene antagonists. In some aspects, small particle 100 may be configured to hold relatively high concentrations of antihistamine(s) 102, and/or may be configured to hold multiple different types/forms of antihistamine(s) 102 simultaneously in order to provide an optimal treatment regimen for one or more allergic reactions/allergies/allergy cascades by maximizing medication varieties and/or dosages while minimizing and/or preventing unwanted side effects that might otherwise be associated therewith.

In order to carry different types/forms of antihistamines 102 at one time while preventing them from interacting with each other, in some aspects, especially when small particle 100 comprises a liposome, small particle 100 may comprise at least two layers. These layers may comprise substantially concentric spheres 104 (shown as spheres 104*a-b* in FIG. 1) separated by dividing layers 106 (shown as dividing layers 106*a-b* in FIG. 1). In some additional aspects, spheres 104 may comprise one or more phospholipids and dividing layers 106 may comprise water. Antihistamine(s) 102 may be at least partially contained within spheres 104 and/or divided layers 106. In still some additional aspects, one or more bifunctional antibodies 202 (not shown in FIG. 1) may be at least partially contained within an outermost sphere 104 of small particle 100. In yet some additional aspects, such outermost sphere 104 may comprise at least of an outer membrane for small particle 100. In still some additional aspects, such membrane may comprise a lipid bilayer. In yet some additional aspects, spheres 104 may comprise elements/substances other than phospholipids and/or dividing layers 106 may comprise other similar dividing elements/substances other than water, as may be apparent to those skilled in the relevant art(s) after reading the description herein. Spheres 104 and/or dividing layers 106 may be configured in various proportions, positions, and/or sizes to optimize effectiveness of storage and/or delivery of antihistamine(s) 102 contained within small particle 100. In an embodiment, element 104*a* is the hydrophobic phase of a liposome (e.g., the inside of a lipid bilayer); element 104*b* is the aqueous core of the liposome; element 106*a* is the outer boundary of the lipid bilayer; and element 106*b* is the inner boundary of the lipid bilayer. When describing various embodiments, the word "sphere" is used in a biological sense (as opposed to a strict mathematical sense); as such, a sphere as described here can have many different shapes that deviate from a mathematical sphere (e.g., a sphere can take any shape that a liposome can take). The shapes described as a "sphere" can also change dynamically, as many chemical and biological molecules fluctuate through an ensemble of shapes.

Nanoparticles (e.g., liposomes) can be configured to have different release properties. For example, some nanoparticles may be configured for an extended release, in other words they may either release antihistamines with different kinetics profiles (e.g., slowly) or they may travel to different portions of a patient (e.g., the respiratory system as opposed to both the respiratory system and systemic circulation). In some embodiments, an extended release nanoparticle is one that has a larger size, which would decrease its probability of reaching the systemic circulation.

In some embodiments, the liposome preparations used are mixtures of unilamelar and multilamellar vesicles (MLV). MIN have several layers, which can be described as an onion structure. This is accomplished by progressively smaller liposomes forming inside the others, which are separated by an aqueous solution. MLV can be loaded with different pharmaceutical ingredients (e.g., antihistamines) so that one vesicle carries, as an example 1, 2, 3, or 4 antihistamines. Unilamelar vesicles may carry one type of antihistamine, but could then be mixed together with other unilamelar vesicles carrying different type of antihistamines, which is to the same effect as MLV.

As regards to lipid compositions of the liposomes, some embodiments use a mix of different types. For the rapid release in the nasal cavity and respiratory tract, an embodiment uses different millimolar ratios of cholesterol and soybean L-infinity-phosphatidylcholine. Another option is dipalmitoylphosphatidylcholine. These chemical compositions are compatible with similar to pulmonary surfactants in the human lung, and do not do not elicit allergy reactions themselves. In order to improve the properties of liposomes, such as increasing the time in circulation (liposomes alone tend to be taken up quickly by immune cells and disappear from circulation), some embodiments use the polymer polyethylene glycol (PEG).

Beyond the chemical composition, depositions can also be controlled by the size of the nanoparticles: larger particles settle more in upper airways, while to reach alveoli the particles less than 10 μm are preferred in some embodiments, or alternatively by particle sizes below 2 μm. Thus, control of the delivery can also be made by mixing different sizes of nanoparticles in specific ratios.

In another form, cyclodexrins can be used to encapsulate and load difficult to load antihistamines. Cyclodexrins are also inert in the respiratory tract.

There are several companies in the USA that are specifically there for contract production and manufacturing of liposomes, as specified by us. Manufacturers use several different methods, broadly categorized as (i) passive loading techniques, and (ii) active loading techniques. Common passive loading techniques include mechanical dispersion (e.g., sonication or extrusion, micro-emulsification, membrane extrusion, and freeze-thaw), solvent dispersion, and detergent removal. In passive loading, the lipid and antihistamine are codispersed in aqueous sterile fluid, and the drug is entrapped in the aqueous fluid as the liposome is being formed, and, based on the specific technique, can achieve up to 90% efficiency.

In active loading techniques, the drugs are loaded into an already formed liposome down a transmembrane pH gradient. The pH outside the nanoparticle allows the antihistamine to be in unionized form, which allows it to cross the lipid membrane into the particle, but once its inside it gets ionized and trapped inside and is only released at specific rates. Any other currently known methods can be used to assemble the nanoparticles with antihistamines in them.

Figure 2:
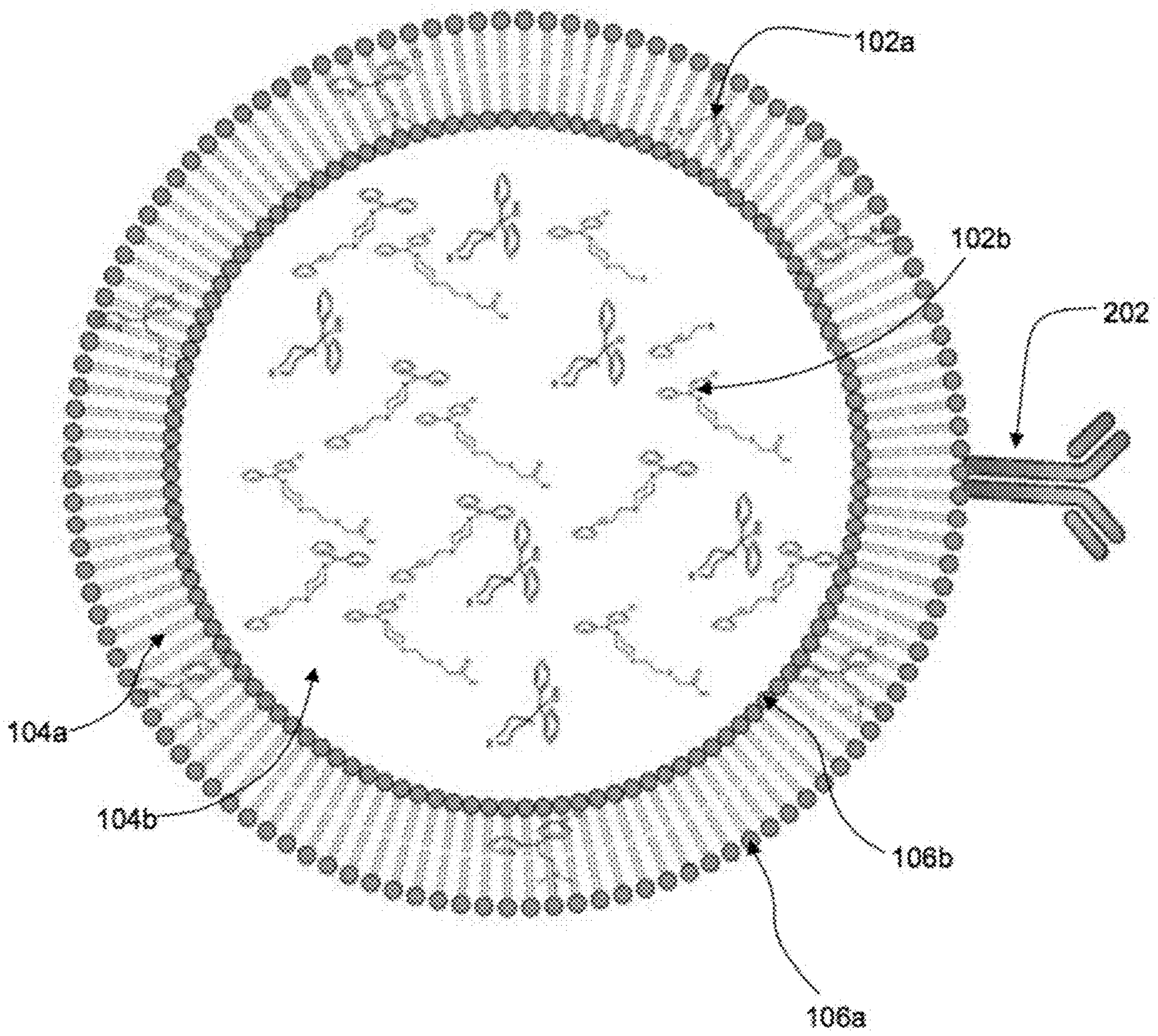
FIG. 2 is a cutaway view of an exemplary small particle integrated with a bifunctional antibody for facilitating the delivery of one or more antihistamines to one or more specific locations within a human body, according to an aspect of the present disclosure.

Referring now to FIG. 2, a cutaway view of an exemplary small particle 100 integrated with a bifunctional antibody 202 for facilitating the delivery of one or more antihistamines 102 (labeled only as antihistamines 102*a-b* in FIG. 2, for clarity) to one or more specific locations within a human body, according to an aspect of the present disclosure, is shown. In some aspects, small particle 100 may be integrated with one or more bifunctional antibodies 202. A given bifunctional antibody 202 may be integrated with small particle 100 via any appropriate means as may be apparent to those skilled in the relevant art(s) after reading the description herein, such as, by way of example and not limitation, via one or more types of chemical bonding. Bifunctional antibody 202 may serve both guiding and blocking functions for small particle 100. Bifunctional antibody 202 may be used separately from small particle 100 or may be attached to/integrated with small particle 100.

Regarding the guiding functions of bifunctional antibody 202, bifunctional antibody 202 may detect and/or seek out FcεRI receptors 304 (not shown in FIG. 2) associated with the surfaces of various types of target cells 302 (not shown in FIG. 2), such as mast cells, basophils, and/or dendritic cells. As a given bifunctional antibody 202 detects and binds to FcεRI receptors 304, it takes along any small particle 100 with which it may have integrated, carrying with it one or more antihistamines 102 that may be at least partially or completely contained within small particle 100 and deliver such antihistamine(s) 102 to the intended targeted locations, regions, processes, functions, diseases, disorders, systems, organs, and/or target cells 302 within the body. Antihistamine(s) 102 may be loaded into small particle 100 via passive or active loading techniques.

In some aspects, one or more small particles 100 may be bound together or otherwise physically and/or chemically connected. In such aspects, a single antibody 202 may be used to guide more than one type of small particle 100 to a targeted location, region, process, function, disease, disorder, system, organ, and/or target cell 302 within the body. In some additional aspects, a single small particle 100 may have more than one bifunctional antibody 202 in order increase the ability of small particle 100 to reach a specific location region, process, function, disease, disorder, system, organ, and/or target cell 302 within the body.

In some aspects, bifunctional antibody 202 may guide small particle 100 to various locations within a human body, such as, by way of example and not limitation, one or more target cells 302, and prevent small particle 100 from traveling across the blood-brain barrier to the central nervous system and/or traveling to other parts of the body that are desired to be secluded from antihistamine(s) 102, thereby minimizing and/or preventing antihistamine(s) 102 within small particle 100 from causing any unwanted side effects to the central nervous system and/or other parts of the body. These unwanted side effects may include, by way of example and not limitation, drowsiness, confusion, blurred vision, difficulty sleeping, nightmares, hallucinations, difficulty emptying the bladder, constipation, and the like. Additionally, because each small particle 100 is directed to one or more locations, regions, processes, functions, diseases, disorders, systems, organs, and/or target cells 302 within the body, the risk of side effects, generally, are minimal in that antihistamine(s) 102 contained within small particle 100 are not released throughout the whole body, but rather are limited in delivery to one or more specific sites where they are released; therefore, several different forms of antihistamine(s) 102 may be administered to a body simultaneously via one or more small particles 100 without incurring the risk of the different forms of antihistamine(s) 102 interacting negatively with each other and/or increasing the toxicity of one another in a way that causes detrimental effects to the body. Furthermore, high concentrations of one or more antihistamines 102 may be delivered to one or more specific areas within the body in order to create high concentrations of antihistamine(s) 102 in such specific localized areas while keeping the overall dosage of antihistamine(s) 102 low and while keeping systemic concentrations low. This is because the targeted nature of the delivery makes it unnecessary to introduce high concentrations of antihistamine(s) 1.02 that have to travel throughout the entire body, including escaping chemical modification by the digestive system and liver, thereby contributing to the mitigation of unwanted side effects. In some additional aspects, small particle 100 may be specifically designed to not be able to travel across the blood-brain barrier in order to provide further protection of the central nervous system from unwanted side effects.

In order to cross link the antibody and liposome, several methods can be used. Indeed several crosslinkers are available for purchase and use. In some embodiments, the approach to form a covalent bond involves reaction of sulfhydryl groups in cysteine regions undergoing a reaction with maleimide groups. First, there is thiolation of the guiding and blocking antibody with 3-(2-pyridyldithio)propionic acid-N-hydroxysuccinimide ester, then deprotection with dithiothreitol (DTT). Maleimide groups can be used to provide activated ends to the liposome, and the final chemical reaction is conjugation to maleimide-derivatized 1,2-distearoyl-sn-glycero-3-phosphoethanolamine (DSPE) or 1,2-dipalmitoyl-sn-glycero-3-phosphoethanolamine (DPPE) on the liposome. As regards to PEG, the methoxy form of PEG has a single hydroxyl group that can be coupled with several entities, including antibodies. Thus, in another form this can be used to bind guiding antibody. Indeed, there are several such methods that can be used, in such a way that the antibody retains its three-dimensional structure so as to allow specificity to its receptor. Any other currently known methods can be used to attach the targeting moiety (e.g., antibody) to the nanoparticles.

Figure 3:
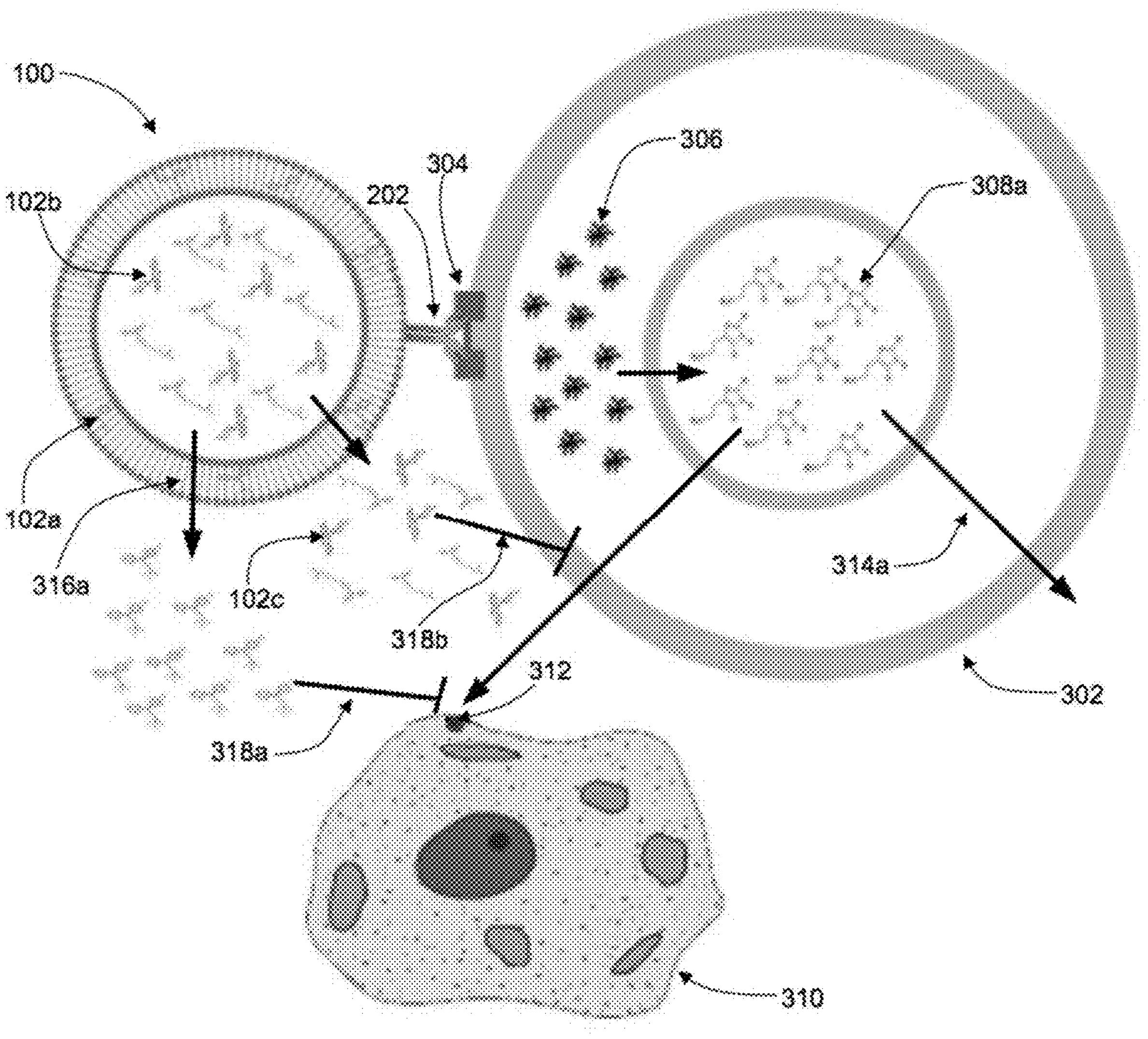
FIG. 3 is a cutaway view of an exemplary small particle integrated with a bifunctional antibody bound to a target cell, according to an aspect of the present disclosure.

Referring now to FIG. 3, a cutaway view of an exemplary small particle 100 integrated with a bifunctional antibody 202 bound to a target cell 302, according to an aspect of the present disclosure, is shown.

Bifunctional antibody 202 may be configured to guide small particle 100 to various types of target cells 302. By way of example and not limitation, a given target cell 302 may comprise a mast cell, a basophil, or a dendritic cell. In some aspects, bifunctional antibody 202 may guide small particle 100 to various other specific locations within a human body, including but not limited to one or more specific organs, one or more specific regions, one or more specific body systems (such as, by way of example and not limitation, the skin), one or more areas in proximity to where one or more specific processes and/or functions are occurring (including areas in proximity to where one or more diseases/disorders are undergoing processes and/or functions), one or more areas in proximity to where one or more substances are being secreted (including substances being secreted due to one or more diseases), and the like.

In order to accomplish its one or more guiding functions, bifunctional antibody 202 may, in some aspects, detect and/or be drawn to one of FcεRI receptors 304 upon the surfaces of one or more target cells 302. Once bifunctional antibody 202 binds to and/or otherwise occupies a given FcεRI receptor 304, bifunctional antibody 202 may also perform one or more blocking functions by preventing IgE antibodies from binding to FcεRI receptors 304. Preventing IgE antibodies from binding to FcεRI receptors 304 on the surfaces of various target cells 302 serves to prevent the cross-linking of the IgE antibodies (the cross linking is represented by element 306 in FIG. 3) as well as the aggregation of FcεRI receptors 304 upon the surfaces of target cells 302. This, in turn, prevents target cells 302, such as mast cells and basophils, from going through the degranulation process that releases histamine molecules 308 (labeled only as histamine molecule 308*a* in FIG. 3, for clarity), leukotrienes, and other inflammatory mediators as shown by directional arrows 314 (labeled only as directional arrow 314*a* in FIG. 3, for clarity). When histamine molecules 308 are not released from target cells 302, they cannot bind to receptors 312 on other cells 310, thereby preventing and/or stopping what would otherwise be an allergic reaction or allergy cascade, as well as the symptoms associated therewith. By way of example and not limitation, other cells 310 may comprise smooth muscle cells, mucous glands, sensory nerve endings, as well as any other appropriate type of human cell as may be apparent to those skilled in the relevant art(s) after reading the description herein.

In some aspects, bifunctional antibody 202 may perform one or more blocking functions without being integrated with any small particles 100. In such aspects, one or more bifunctional antibodies 202 may be delivered to a human body via any of the appropriate inhalational delivery devices and/or methods as may be apparent to those skilled in the relevant art(s) after reading the description herein. In some aspects, by way of example and not limitation, the bifunctional antibody 202 alone or in combination with other substances may also be delivered intravenously to stop the allergy cascade.

In order to prevent or stop histamine molecules 308, leukotrienes, or any other similar inflammatory mediators from being released by a target cell 302, antihistamine(s) 102 (labeled only as antihistamines 102*a-c* in FIG. 3, for clarity) may be released from small particle 100 as shown by directional arrows 316 (labeled only as directional arrow 316*a* in FIG. 3, for clarity) in order to provide rapid and/or substantially instantaneous counter effects for an allergic reaction or allergy cascade that may be about to start or that is already in progress, such rapid and/or substantially instantaneous effects occurring within a few minutes, seconds, or less of within the time small particle 100 is first introduced into the body. In some aspects, antihistamine(s) 102 may be released in relatively high quantities and/or concentrations. In some additional aspects, more than one form of antihistamine 102 may be at least partially contained within and released by any given small particle 100. In still some additional aspects, the time and/or duration of release of antihistamine(s) 102 from small particle 100 may be altered by using different variations, chemical composition, sizes, and/or configurations of small particle 100. By way of example and not limitation, the time and/or duration of antihistamine 102 release from small particle 100 may be adjusted by altering how quickly small particle 100 breaks down, dissolves, or otherwise releases and/or exposes antihistamine(s) 102 within it to a given body location, region, process, function, disease, disorder, system, organ, and/or target cell 302 as may be apparent to those skilled in the relevant art(s) after reading the description herein.

By way of example and not limitation, antihistamine(s) 102 may serve as $H_1$ antagonists, thereby blocking the interaction of histamine molecules 308 with receptors 312 on other cells 310, including $H_1$ receptors, as indicated by blocking line 318*a*, in order to prevent other cells 310 from expressing the symptoms of and/or from experiencing one or more actions associated with an allergic reaction or allergy cascade, such as, by way of example and not limitation, inflammation. Additionally, especially when target cell 302 is a mast cell or basophil, antihistamine(s) 102 may serve as mast cell or basophil stabilizers, respectively, thereby preventing the release of histamine molecules 308 from target cell 302 by preventing the degranulation process, as indicated by blocking arrow 318*b*. Other types of antihistamine(s) 102 may be released from small particle 100 as may be apparent to those skilled in the relevant art(s) after reading the description herein, including, but not limited to corticosteroids and leukotriene receptor antagonists. The targeted delivery of multiple forms of antihistamines 102 via small particle(s) 100 allows for different steps in the allergy cascade to be blocked simultaneously, without causing unwanted side effects associated with administering and mixing multiple antihistamines 102 within systemic circulation 416 (not shown in FIG. 3), without the additive adverse events effects associated with multiple antihistamines simultaneously crossing the blood brain barrier.

In some aspects, one or more antihistamines 102 may enter target cell 302 when an outer layer and/or membrane of small particle 100 fuses with an outer layer and/or membrane of target cell 302, thereby allowing antihistamine(s) 102 to traverse target cell 302 membranes that they may otherwise not be able to pass through.

Figure 4:
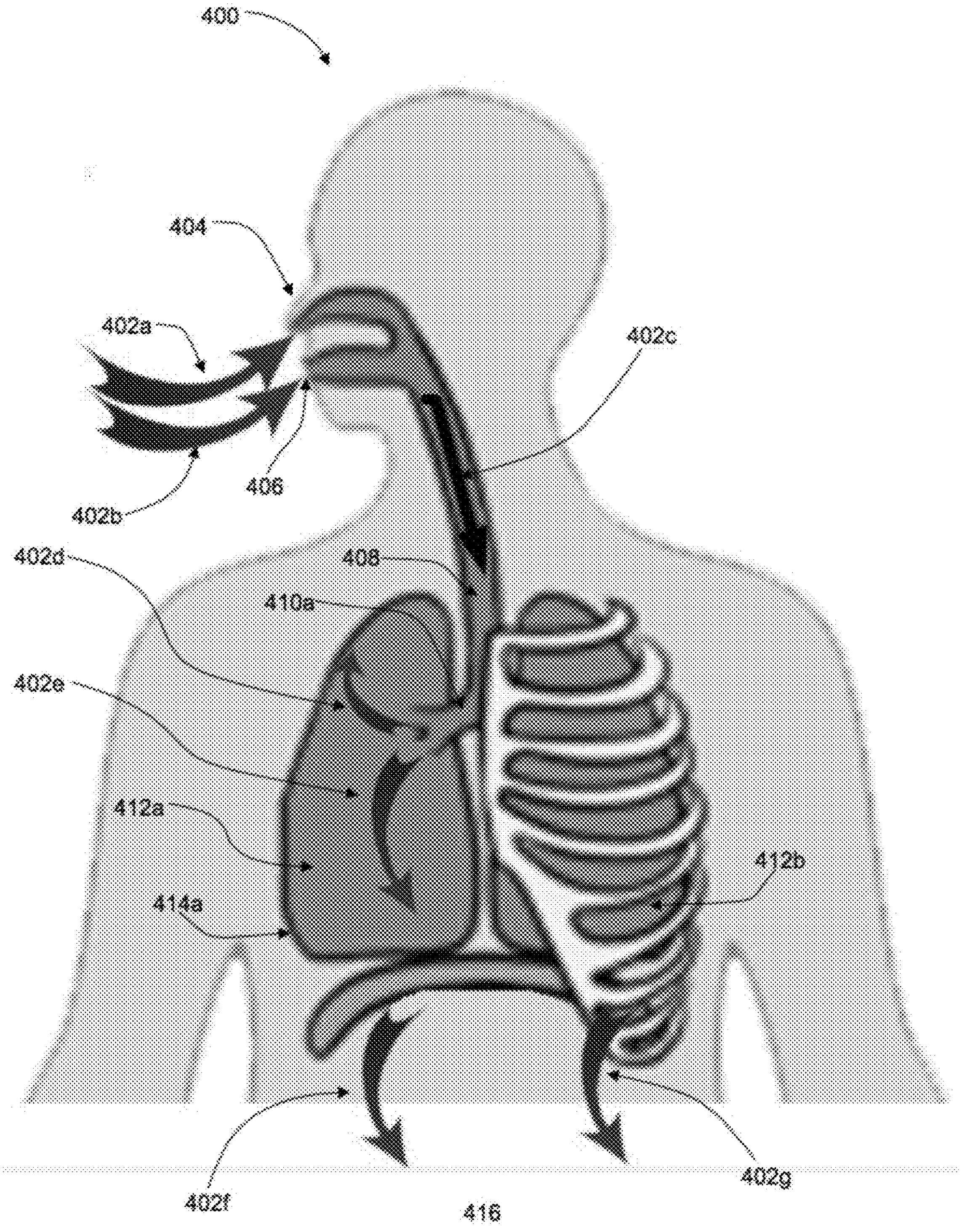
FIG. 4 is a cutaway view of a human respiratory system capable of receiving and/or processing one or more small particles integrated with one or more bifunctional antibodies configured to facilitate the delivery of one or more antihistamines to a human body, according to an aspect of the present disclosure.

Referring now to FIG. 4, a cutaway view of a human respiratory system 400 capable of receiving and/or processing one or more small particles 100 (not shown in FIG. 4) integrated with one or more bifunctional antibodies 202 (not shown in FIG. 4) configured to facilitate the delivery of one or more antihistamines 102 (not shown in FIG. 4) to a human body, according to an aspect of the present disclosure, is shown.

One or more small particles 100 may enter and travel through human respiratory system 400 as indicated, by way of example and not limitation, by directional arrows 402. (shown as directional arrows 402*a-g* in FIG. 4). Human respiratory system 400 may comprise upper and lower airways and may be accessed by one or more small particles 100 via inhalational and/or intranasal means. In some aspects, one or more small particles 100 may enter the body via a human nose 404, as indicated by directional arrow 402*a*, or as indicated by directional arrow 402*b*, such as, by way of example and not limitation, via inhalation. Another mode of entry that is possible is through mouth 406. Small particles 100 may be inhaled, by way of example and not limitation, in a dry powder form or as one or more aerosol droplets, such as, by way of example and not limitation, those created by a nebulization process. Small particles 100 may also be inhaled in any other appropriate form as may be apparent to those skilled in the relevant art(s) after reading the description herein. Other appropriate delivery devices, techniques, and/or means may also be used as may be apparent to those skilled in the relevant art(s) after reading the description herein.

Small particle(s) 100 that are inhaled via human respiratory system 400 may travel through trachea 408 as indicated by directional arrow 402*c*, bronchi 410 (shown only as bronchus 410*a* in FIG. 4), and into lungs 412 (labeled as lungs 412*a-b* in FIG. 4) as indicated by directional arrows 402*d-e*. Some small particles 100 may be configured to pass through the surfaces 414 (labeled only as surface 414*a* in FIG. 4, for clarity) of one or both lungs 412 and make their way into systemic circulation (represented by region 416 in FIG. 4) as indicated by directional arrows 402*f-g*.

The final destination of one or more small particles 100 may be dependent upon their size and chemical composition. Larger small particles 100 may comprise a first variation of small particles 100 and may be configured to stay relatively close to and detect and bind to one or more target cells 302 near their point of entry, such as within lungs 412, bronchi 410, or the nasopharynx and/or nasal cavity (not labeled in FIG. 4) just beyond nose 404, and/or upon one or more inner surfaces thereof, in order to provide fast, substantially instantaneous targeted relief for allergy symptoms, such as within a few minutes, seconds, or less of being introduced into human respiratory system 400. Smaller small particles 100 may comprise a second variation of small particles 100 and may be configured to travel to further, more distal regions within lungs 412 and/or human respiratory system 400, generally, including but not limited to alveoli (not shown in FIG. 4), alveolar ducts (not shown in FIG. 4), and/or respiratory bronchioles (not shown in FIG. 4), and/or upon one or more inner surfaces thereof, thereby serving to provide more long-lasting relief for allergy symptoms and/or to target other parts of respiratory system 400. Smaller small particles 100 may also be configured to pass through one or more surfaces 414 of one or both lungs 412, or one or more surfaces of other portions of human respiratory system 400 such as, by way of example and not limitation, via absorption, in order to enter systemic circulation 416 (such as, by way of example and not limitation, via capillaries (not shown in FIG. 4)) in order to target one or more other parts of the body, including other locations, regions, processes, functions, diseases, disorders, systems, organs, and/or target cells 302 (not shown in FIG. 4), and the like. In some aspects, this absorption may occur relatively immediately upon small particle(s) 100 of the second variation entering respiratory system 400.

In some aspects, one type of small particles 100 may contain higher concentrations of antihistamine(s) 102 than a second type of small particles 100. In some additional aspects, first type of small particles 100 may comprise a 0% absorption rate into systemic circulation 416 as they may remain within human respiratory system 400, while a second type of small particles 100 may be more than an 80% absorbed into systemic circulation 416, which may, by way of example and not limitation, be accomplished via absorption of small particles 100 into the systemic circulation 416 through one or more surfaces 414 of one or both lungs 412 or through one or more nasal structures and/or other surfaces associated with human respiratory system 400. Different variations of small particles 100 may comprise different particle types, compositions, and/or may comprise different amounts, concentrations, and/or forms of antihistamine(s) 102.

In some aspects, at least two variations of small particles 100 may be administered to an individual simultaneously as a mixture, in order to provide a combination of fast relief and long lasting relief of allergy symptoms.

Figure 5A:
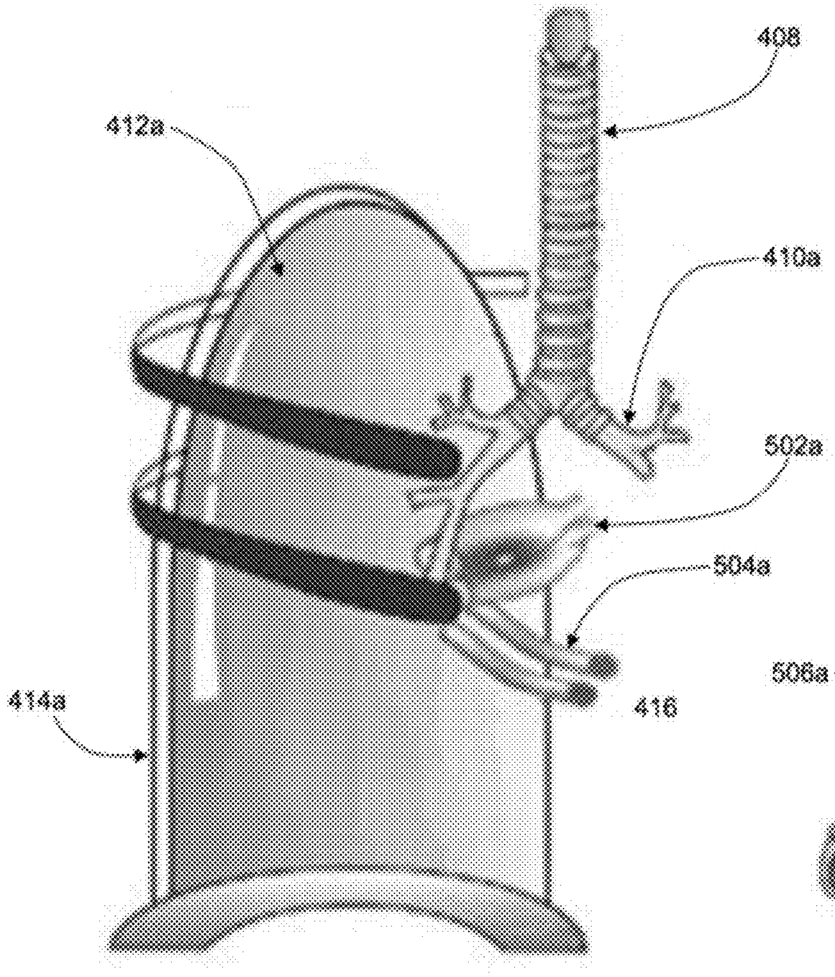
FIGS. 5A-5C are cutaway views of various portions of a human respiratory system capable of receiving and/or processing one or more small particles integrated with one or more bifunctional antibodies configured to facilitate the delivery of one or more antihistamines to a human body, according to one or more aspects of the present disclosure.
Figure 5B:
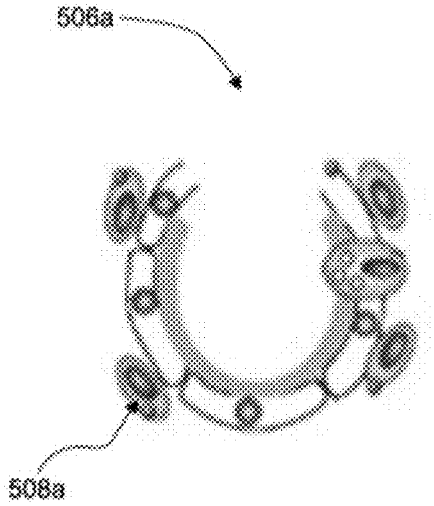
Figure 5C:
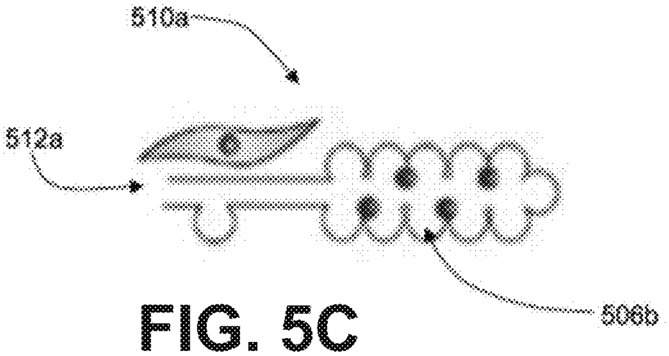

Referring now to FIGS. 5A-5C, cutaway views of various portions of a human respiratory system 400 (not completely shown in FIGS. 5A-5C) capable of receiving and/or processing one or more small particles 100 (not shown in FIGS. 5A-5C) integrated with one or more bifunctional antibodies 202 (not shown in FIGS. 5A-5C) configured to facilitate the delivery of one or more antihistamines 102 (not shown in FIGS. 5A-5C) to a human body, according to one or more aspects of the present disclosure, are shown. Also shown in this figure are blood vessels 502*a*, other blood vessels 504*a*, and alveolus cross section 508*a*.

In order to facilitate delivery of one or more small particles 100 into systemic circulation 416, one or more small particles 100 that leave one or both lungs 412 (shown only as lung 412*a* in FIG. 5A) via a lung surface 414 (labeled only as lung surface 414*a* in FIG. 5A, for clarity) may be taken to other parts of the body via pulmonary circulation.

Figure 6:
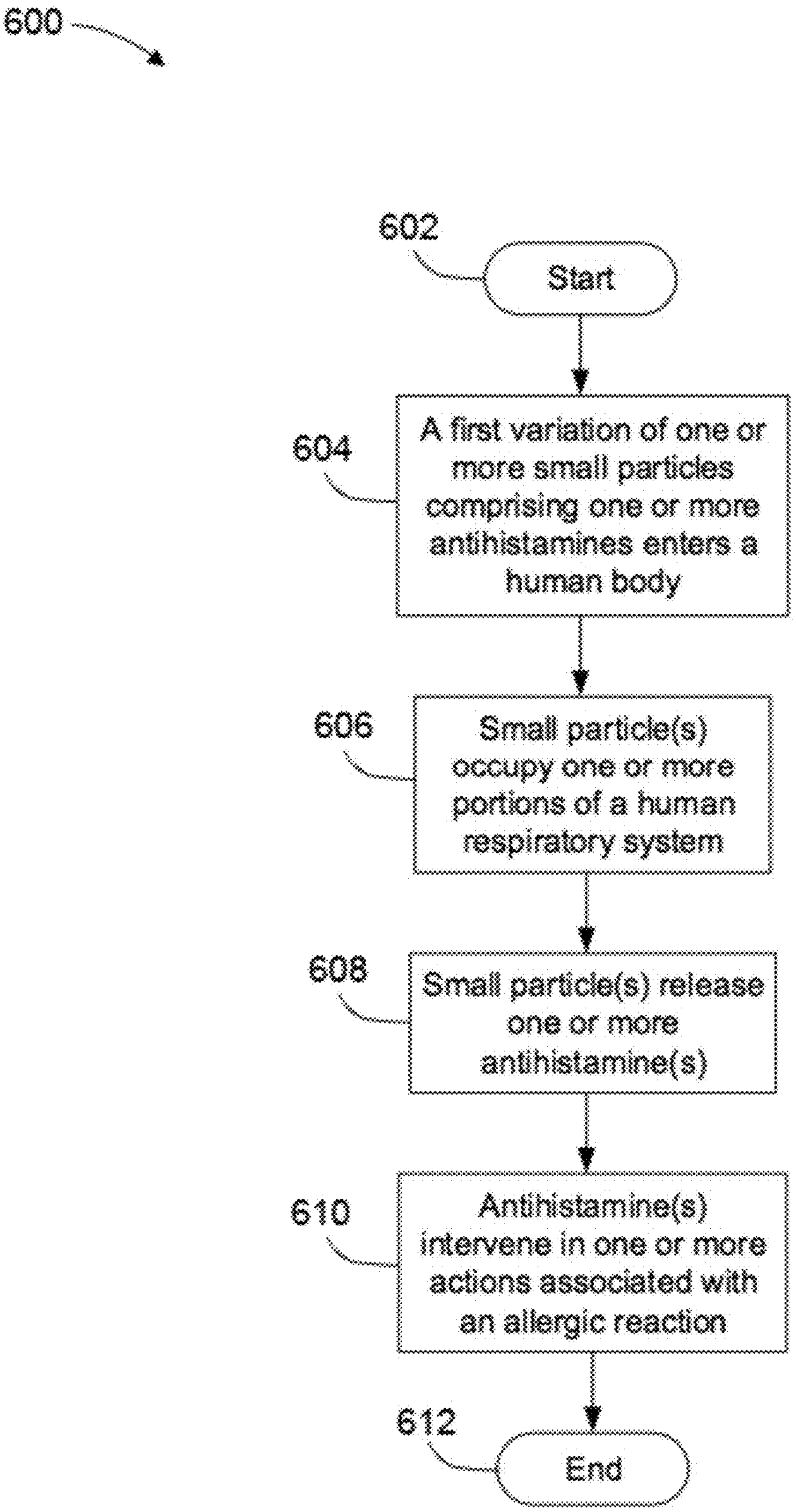
FIG. 6 is a flowchart illustrating an exemplary process for intervening in one or more actions associated with an allergic reaction within a human body using a first variation of one or more small particles comprising one or more antihistamines, according to an aspect of the present disclosure.

Referring now to FIG. 6, a flowchart illustrating an exemplary process 600 for intervening in one or more actions associated with an allergic reaction within a human body using a first variation of one or more small particles 100 (not shown in FIG. 6) comprising one or more antihistamines 102 (not shown in FIG. 6), according to an aspect of the present disclosure, is shown.

Process 600 begins at step 602 with control passing immediately to step 604.

At step 604, one or more small particles 100 of the first variation enter a human body. As previously discussed, in some aspects, small particle(s) 100 of the first variation may comprise a relatively larger size than small particle(s) 100 of the second variation. In some additional aspects, small particle(s) 100 of the first variation that enter the human body at step 604 may comprise one or more antihistamines 102. Small particles(s) 100 of the first variation may enter the human body via human nose 404 (not shown in FIG. 6), human respiratory system (not shown in FIG. 6), or by being absorbed by/into/through or injected into human veins in emergencies. To facilitate entry of small particle(s) 100 of the first variation into the human body, one or more delivery means may be used as may be apparent to those skilled in the relevant art(s) after reading the description herein.

Once small particle(s) 100 of the first variation have entered the human body, process 600 proceeds to step 606.

At step 606, small particle(s) 100 of the first variation find their way to and occupy one or more portions of human respiratory system 400 (not shown in FIG. 6). By way of example and not limitation, small particle(s) 100 of the first variation may occupy one or more portions of the nasal cavity, one or more portions of trachea 408, one or more bronchi 410, one or both of lungs 412, one or more alveoli (not shown in FIGS. 4 and 5), one or more alveolar ducts, and/or one or more respiratory bronchioles, as well as any other appropriate portion of human respiratory system 400 as may be apparent to those skilled in the relevant art(s) after reading the description herein. In some aspects, small particle(s) 100 of the first variation may travel to different portions of human respiratory system 400 depending on their size. By way of example and not limitation, larger small particle(s) 100 of the first variation may remain within the nasal cavity, trachea 408, bronchi 410, and/or lungs 412, while smaller small particles 100 of the first variation may be able to travel to alveoli 506, alveolar ducts 510, and respiratory bronchioles 512, and the like.

In some aspects, one or more bifunctional antibodies 202 may guide small particle(s) 100 of the first variation on where to go within human respiratory system 400. By way of example and not limitation, small particle(s) 100 of the first variation may be directed to one or more specific locations, regions, processes, functions, diseases, disorders, target cells 302, and the like.

Once small particle(s) 100 of the first variation reach appropriate location(s) within human respiratory system 400, process 600 proceeds to step 608.

At step 608, small particle(s) 100 of the first variation may release one or more antihistamines 102 from within them in the vicinity of mast cells and basophils. In some aspects, one or more outer surfaces and/or membranes of small particle(s) 100 of the first variation may break down and/or otherwise decompose in order to release and/or expose the one or more antihistamines 102. In some additional aspects, small particle(s) 100 of the first variation may fuse with one or more target cells 302 and/or other cells 310 (not shown in FIG. 6). Upon fusing with such cells, one or more outer surfaces and/or membranes of small particle(s) 100 of the first variation may open up or otherwise alter in structure and/or composition in order to allow one or more antihistamine(s) 102 to leave small particle(s) 100 and enter target cell(s) 302 and/or other cell(s) 310; or, in some aspects, antihistamine(s) 102 may pass through outer surface(s)/membrane(s) of small particle(s) 100 of the first variation and into target cell(s) 302, other cell(s) 310, or any other appropriate area, region, system, organ, or cell as may be apparent to those skilled in the relevant art(s) after reading the description herein.

Once antihistamine(s) 102 have been released from small particle(s) 100 of the first variation, process 600 proceeds to step 610.

At step 610, antihistamine(s) 102 that have been released intervene in one or more actions associated with an allergic reaction. By way of example and not limitation, antihistamine(s) 102 may comprise one or more mast cell stabilizers, basophil stabilizers, $H_1$ antagonists, corticosteroids, leukotriene receptor antagonists, or any combination thereof.

Mast cell stabilizers and basophil stabilizers may function by blocking one or more calcium channels within mast cells and basophils, respectively, that are needed for cell degranulation. If mast cells and/or basophils are not able to go through the degranulation process, then they do not release any histamine molecules 308 (not shown in FIG. 6), $H_1$ antagonists may function by blocking the interaction of histamine molecules 308 with receptors 312 (not shown in FIG. 6) on various other cells 310, including $H_1$ receptors, in order to prevent other cells 310 from expressing the symptoms of and/or experiencing one or more actions associated with an allergic reaction or allergy cascade, such as, by way of example and not limitation, inflammation. By way of example and not limitation, other cells 310 may comprise smooth muscle cells, mucous glands, sensory nerve endings, as well as any other appropriate type of cell as may be apparent to those skilled in the relevant art(s) after reading the description herein. Corticosteroids may function by preventing or minimizing inflammation at different sites within the body, while leukotriene receptor antagonists may function by blocking one or more chemical reactions that may lead to inflammation within the various airways of human respiratory system 400, including but not limited to the nasal cavity, trachea 408, one or more bronchi 410, one or both of lungs 412, one or more alveoli, one or more alveolar ducts one or more respiratory bronchioles and the like.

Once at least one action associated with an allergic reaction has been prevented and/or stopped, process 600 proceeds to step 612.

At step 612 process 600 is terminated and process 600 ends.

Figure 7:
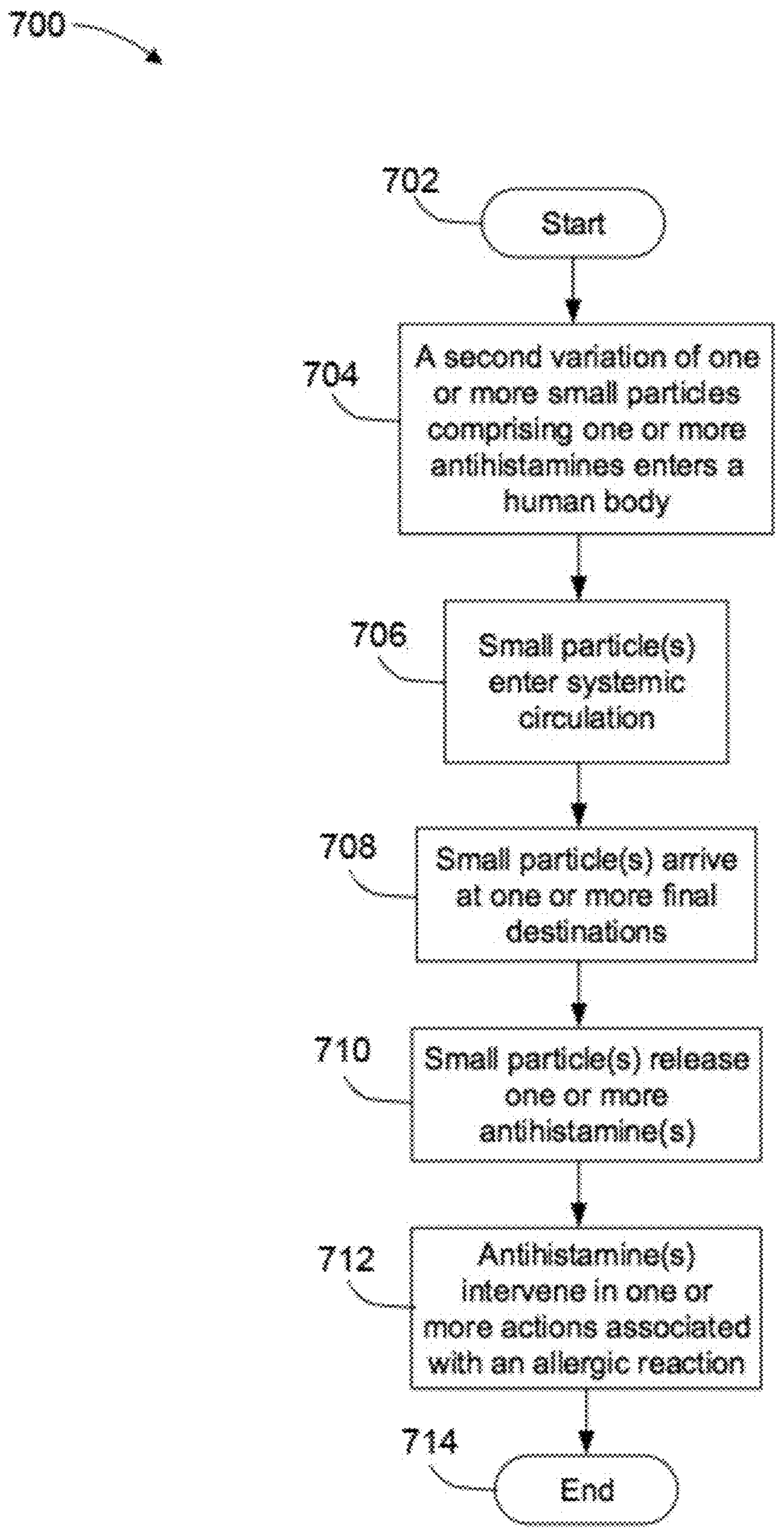
FIG. 7 is a flowchart illustrating an exemplary process for intervening in one or more actions associated with an allergic reaction within a human body using a second variation of one or more small particles comprising one or more antihistamines, according to an aspect of the present disclosure.

Referring now to FIG. 7, a flowchart illustrating an exemplary process 700 for intervening in one or more actions associated with an allergic reaction within a human body using a second variation of one or more small particles 100 (not shown in FIG. 7) comprising one or more antihistamines 102 (not shown in FIG. 7), according to an aspect of the present disclosure, is shown.

Process 700 begins at step 702 with control passing immediately to step 704.

At step 704, one or more small particles 100 of the second variation enter a human body. As previously discussed, in some aspects, small particle(s) 100 of the second variation may comprise a relatively smaller size than small particle(s) 100 of the first variation or different chemical composition. In some additional aspects, small particle(s) 100 of the second variation that enter the human body at step 704 may comprise one or more antihistamines 102 (not shown in FIG. 7). Small particles(s) 100 of the second variation may enter the human body via human nose 404 (not shown in FIG. 7), inhalation into the human lung (not shown in FIG. 7), or intravenous injection in emergencies, by appropriate delivery devices/means as may be apparent to those skilled in the relevant art(s) after reading the description herein.

Once small particle(s) 100 of the second variation have entered the human body, process 700 proceeds to step 706.

At step 706, small particle(s) 100 of the second variation enter systemic circulation 416 (not shown in FIG. 7). In some aspects, small particle(s) 100 of the second variation may enter systemic circulation 416 via intranasal means, by the absorption of small particle(s) 100 of the second variation into systemic circulation 416 through one or more surfaces 414 (not shown in FIG. 7) of one or both lungs 412 (not shown in FIG. 7), through one or more surfaces associated with any other portion of human respiratory system 400 (not shown in FIG. 7), and/or through one or more nasal structures associated with human respiratory system 400.

Once small particle(s) 100 of the second variation reach systemic circulation 416, process 700 proceeds to step 708.

At step 708, small particle(s) 100 of the second variation travel to one or more final destinations within the body via systemic circulation 416. By way of example and not limitation, such final destinations may comprise one or more locations, regions, processes, functions, diseases, disorders, systems, organs, target cells 302 (not shown in FIG. 7), other cells 310 (not shown in FIG. 7) and the like within the body. In some aspects, one or more bifunctional antibodies 202 (not shown in FIG. 7) may guide small particle(s) 100 of the second variation on where to go within the body and guide them to one or more specific locations, regions, processes, functions, diseases, disorders, systems, organs, target cells 302, and the like.

Once small particle(s) 100 of the second variation reach appropriate location(s) within the human body, process 700 proceeds to step 710.

At step 710, small particle(s) 100 of the second variation release one or more antihistamines 102 from within them. In some aspects, one or more outer surfaces and/or membranes of small particle(s) 100 of the second variation may break down and/or otherwise decompose in order to release and/or otherwise expose the one or more antihistamines 102. In some additional aspects, small particle(s) 100 of the second variation may fuse with one or more target cells 302 and/or other cells 310. Upon fusing with such cells, one or more outer surfaces and/or membranes of small particle(s) 100 of the second variation may open up or otherwise alter in structure and/or composition in order to allow one or more antihistamine(s) 102 to leave small particles(s) 100 and enter target cell(s) 302 and/or other cell(s) 310; or, in some aspects, antihistamine(s) 102 may pass through outer surface(s)/membrane(s) of small particle(s) 100 and into target cell(s) 302, other cell(s) 310, or any other appropriate area, region, system, organ, or cell as may be apparent to those skilled in the relevant art(s) after reading the description herein.

Once antihistamine(s) 102 have been released from small particle(s) 100 of the second variation, process 700 proceeds to step 712.

At step 712, antihistamine(s) 102 intervene in one or more actions associated with an allergic reaction. By way of example and not limitation, antihistamine(s) 102 may comprise one or more mast cell stabilizers, basophil stabilizers, $H_1$ antagonists, corticosteroids, leukotriene receptor antagonists, or any combination thereof.

Mast cell stabilizers and basophil stabilizers may function by blocking one or more calcium channels within mast cells and basophils, respectively, that are needed for cell degranulation. If mast cells and/or basophils are not able to go through the degranulation process, then they do not release any histamine molecules 308 (not shown in FIG. 7). $H_1$ antagonists may function by blocking the interaction of histamine molecules 308 with receptors 312 (not shown in FIG. 7) on various other cells 310, including $H_1$ receptors, in order to prevent other cells 310 from expressing the symptoms of and/or experiencing one or more actions associated with an allergic reaction or allergy cascade, such as, by way of example and not limitation, inflammation. By way of example and not limitation, other cells 310 may comprise smooth muscle cells, mucous glands, sensory nerve endings, as well as any other appropriate type of cell as may be apparent to those skilled in the relevant art(s) after reading the description herein. Corticosteroids may function by preventing or minimizing inflammation at different sites within the body, while leukotriene receptor antagonists may function by blocking one or more chemical reactions that may lead to inflammation within the various airways of human respiratory system 400, including but not limited to the nasal cavity, trachea 408 (not shown in FIG. 7), one or more bronchi 410 (not shown in FIG. 7), one or both of lungs 412, one or more alveoli (not shown in FIG. 7), one or more alveolar ducts (not shown in FIG. 7), one or more respiratory bronchioles (not shown in FIG. 7), and the like.

Once at least one action associated with an allergic reaction has been prevented and/or stopped, process 700 proceeds to step 714.

At step 714 process 700 is terminated and process 700 ends.

Figure 8:
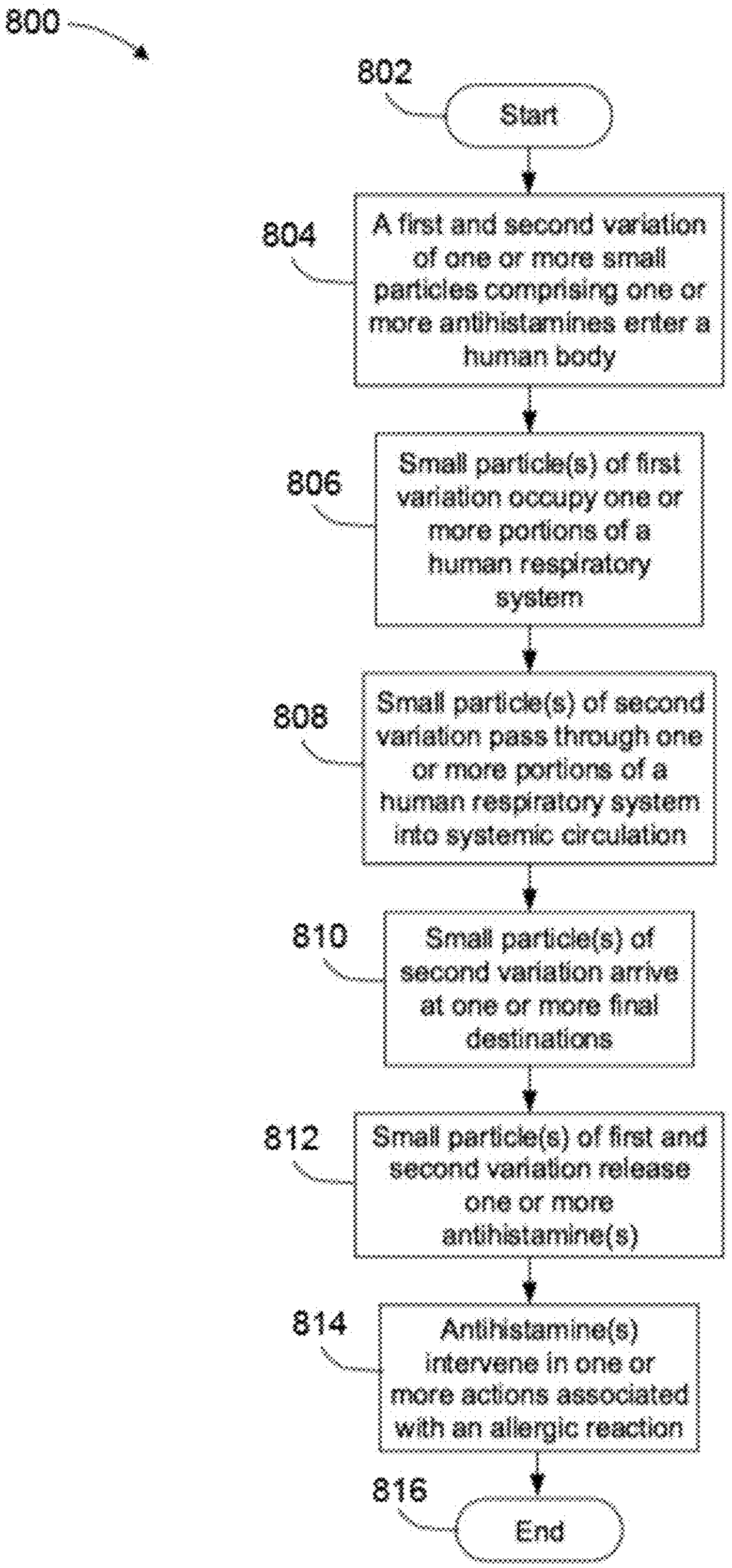
FIG. 8 is a flowchart illustrating an exemplary process for intervening in one or more actions associated with an allergic reaction within a human body using a first variation and a second variation of one or more small particles comprising one or more antihistamines, according to an aspect of the present disclosure.

Referring now to FIG. 8, a flowchart illustrating an exemplary process 800 for intervening in one or more actions associated with an allergic reaction within a human body using a first variation and a second variation of one or more small particles 100 (not shown in FIG. 8) comprising one or more antihistamines 102 (not shown in FIG. 8), according to an aspect of the present disclosure, is shown.

Process 800 begins at step 802 with control passing immediately to step 804.

At step 804, one or more small particles 100 of the first variation and the second variation enter a human body. As previously discussed, in some aspects, small particle(s) 100 of the first variation may comprise a relatively larger size than small particle(s) 100 of the second variation or a different chemical composition. In some additional aspects, small particle(s) 100 of the first and second variations that enter the human body at step 804 may carry a load of one or more antihistamines 102. Small particles(s) 100 of the first and second variations may enter the human body via human nose 404 (not shown in FIG. 8), the human respiratory system (not shown in FIG. 8), or intravenous injection, as well as any other appropriate delivery devices/means as may be apparent to those skilled in the relevant art(s) after reading the description herein.

Once small particle(s) 100 of the first and second variations have entered the human body, process 800 proceeds to step 806.

At step 806, small particle(s) 100 of the first variation find their way to and occupy one or more portions of human respiratory system 400 (not shown in FIG. 8). By way of example and not limitation, small particle(s) 100 of the first variation may occupy one or more portions of the nasal cavity, one or more portions of trachea 408 (not shown in FIG. 8), one or more bronchi 410 (not shown in FIG. 8), one or both of lungs 412 (not shown in FIG. 8), one or more alveoli (not shown in FIG. 8), one or more alveolar ducts (not shown in FIG. 8), and/or one or more respiratory bronchioles (not shown in FIG. 8), as well as any other appropriate portion of human respiratory system 400 as may be apparent to those skilled in the relevant art(s) after reading the description herein. In some aspects, small particle(s) 100 of the first variation may travel to different portions of human respiratory system 400 depending on their size. By way of example and not limitation, larger small particles 100 of the first variation may remain within the nasal cavity, trachea 408, bronchi 410, and/or lungs 412, while smaller small particles 100 of the first variation may be able to travel to alveoli alveolar ducts, respiratory bronchioles, and the like.

In some aspects, one or more bifunctional antibodies 202 (not shown in FIG. 8) may guide small particle(s) 100 of the first variation on where to go within human respiratory system 400. By way of example and not limitation, small particle(s) 100 of the first variation may be directed to one or more specific locations, regions, processes, functions, diseases, disorders, systems, organs, target cells 302 (not shown in FIG. 8), and the like.

In some aspects, step 806 may occur substantially simultaneously as step 808. In some additional aspects, step 806 may occur just before step 808 or just after step 808, or at any other appropriate time as may be apparent to those skilled in the relevant art(s) after reading the description herein.

At step 808, small particle(s) 100 of the second variation enter systemic circulation 416 (not shown in FIG. 8). In some aspects, small particle(s) 100 of the second variation may enter systemic circulation 416 via intranasal means, by being absorbed into systemic circulation 416 through one or more surfaces 414 of one or both lungs 412, and/or through one or more nasal structures associated with human respiratory system 400. In some additional aspects, small particle(s) 100 of the second variation may reach systemic circulation 416 by being injected into human veins.

Once small particle(s) 100 of the second variation reach systemic circulation 416, process 800 proceeds to step 810.

At step 810, small particle(s) 100 of the second variation travel to one or more final destinations within the body via systemic circulation 416. By way of example and not limitation, such final destinations may comprise one or more locations, regions, processes, functions, diseases, disorders, systems, organs, target cells 302, other cells 310 (not shown in FIG. 8), and the like within the body. In some aspects, one or more bifunctional antibodies 202 may guide small particle(s) 100 of the second generation where to go within the body and guide them to one or more specific locations, regions, processes, functions, diseases, disorders, systems, organs, target cells 302, and the like. Relative order of steps 806 and 810 may be reversed.

Once small particle(s) 100 of the second variation reach appropriate location(s) within the human body, process 800 proceeds to step 812. In some aspects, small particle(s) 100 of the first variation proceed to step 812 immediately after step 806. In some additional aspects, small particle(s) 100 of the first variation do not proceed to step 812 until after step 810 has been completed. In still some additional aspects, steps 806, 808, and/or 810 occur substantially simultaneously and/or with a minimal amount of time lapse between them.

At step 812, small particle(s) 100 of both the first and second variations release one or more antihistamines 102 from within them. In some aspects, one or more outer surfaces and/or membranes of small particle(s) 100 of the first and second variations may break down and/or otherwise decompose in order to release and/or expose the one or more antihistamines 102. In some additional aspects, small particle(s) 100 of the first and second variations may fuse with one or more target cells 302 and/or other cells 310. Upon fusing with such cells, one or more outer surfaces and/or membranes of small particle(s) 100 of the first and second variations may open up or otherwise alter in structure and/or composition in order to allow one or more antihistamine(s) 102 to leave small particle(s) 100 and enter target cell(s) 302 and/or other cell(s) 310; or, in some aspects, antihistamine(s) 102 may pass through outer surface(s)/membrane(s) of small particle(s) 100 and into target cell(s) 302, other cell(s) 310, or any other appropriate area, region, system, organ, or cell as may be apparent to those skilled in the relevant art(s) after reading the description herein.

Once antihistamine(s) 102 have been released from small particle(s) 100 of the first and second variations, process 800 proceeds to step 814. Alternatively, release from the first and second variations can proceed as separate parallel processes, without needing both to be complete before step 814.

At step 814, antihistamine(s) 102 intervene in one or more actions associated with an allergic reaction. By way of example and not limitation, antihistamine(s) 102 may comprise one or more mast cell stabilizers, basophil stabilizers, $H_1$ antagonists, corticosteroids, leukotriene receptor antagonists, or any combination thereof.

Mast cell stabilizers and basophil stabilizers may function by blocking one or more calcium channels within mast cells and basophils, respectively, that are needed for cell degranulation. If mast cells and/or basophils are not able to go through the degranulation process, then they do not release any histamine molecules 308 (not shown in FIG. 8). $H_1$ antagonists may function by blocking the interaction of histamine molecules 308 with receptors 312 (not shown in FIG. 8) on various other cells 310, including $H_1$ receptors, in order to prevent other cells 310 from expressing the symptoms of and/or experiencing one or more actions associated with an allergic reaction or allergy cascade, such as, by way of example and not limitation, inflammation. By way of example and not limitation, other cells 310 may comprise smooth muscle cells, mucous glands, sensory nerve endings, as well as any other appropriate type of cell as may be apparent to those skilled in the relevant art(s) after reading the description herein. Corticosteroids may function by preventing or minimizing inflammation at different sites within the body, while leukotriene receptor antagonists may function by blocking one or more chemical reactions that may lead to inflammation within the various airways of human respiratory system 400, including but not limited to the nasal cavity, trachea 408, one or more bronchi 410, one or both of lungs 412, one or more alveoli, one or more alveolar ducts, one or more respiratory bronchioles, and the like.

Once at least one action associated with an allergic reaction has been prevented and/or stopped, process 800 proceeds to step 816.

At step 816, process 800 is terminated and process 800 ends.

Figure 9:
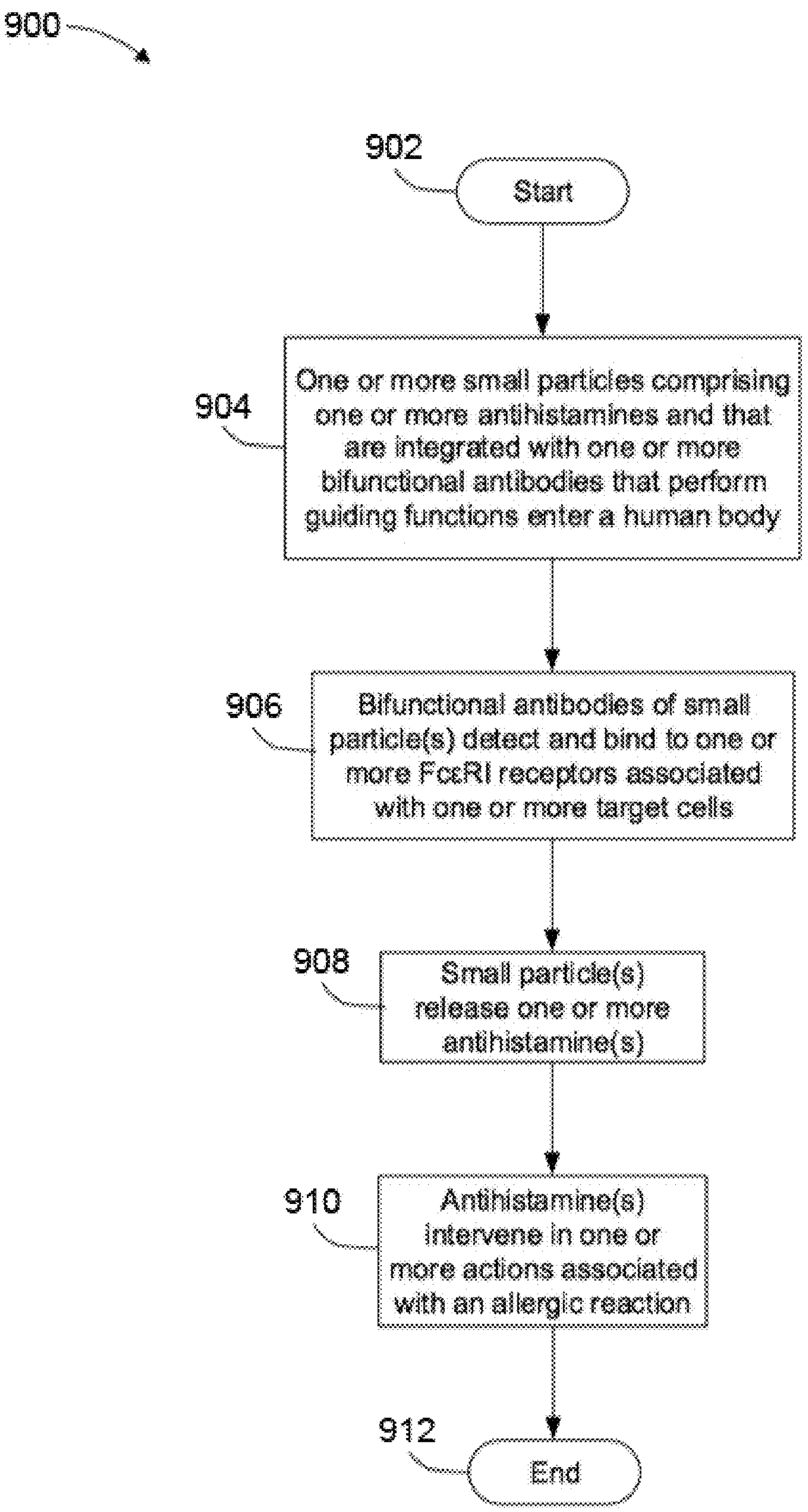
FIG. 9 is a flowchart illustrating an exemplary process for intervening in one or more actions associated with an allergic reaction within a human body using one or more small particles comprising one or more antihistamines, wherein the one or more small particles are integrated with one or more bifunctional antibodies that perform guiding functions, according to an aspect of the present disclosure.

Referring now to FIG. 9, a flowchart illustrating an exemplary process 900 for intervening in one or more actions associated with an allergic reaction within a human body using one or more small particles 100 (not shown in FIG. 9) comprising one or more antihistamines 102 (not shown in FIG. 9), wherein the one or more small particles 100 are integrated with one or more bifunctional antibodies 202 (not shown in FIG. 9) that perform guiding functions, according to an aspect of the present disclosure, is shown.

Process 900 begins at step 902 with control passing immediately to step 904.

At step 904, one or more small particles 100 that are integrated with one or more bifunctional antibodies 202 that perform guiding functions enter a human body. Small particle(s) 100 may be of the first and/or second variation. As previously discussed, in some aspects, small particle(s) 100 of the first variation may comprise a relatively larger size than small particle(s) 100 of the second variation. In some additional aspects, small particle(s) 100 that enter the human body at step 904 may comprise one or more antihistamines 102. Small particles(s) 100 may enter the human body via human nose 404 (not shown in FIG. 9), human respiratory system (not shown in FIG. 9), or human pulmonary system, or intravenous injection, as well as any other appropriate delivery devices/means as may be apparent to those skilled in the relevant art(s) after reading the description herein.

Once small particle(s) 100 have entered the human body, process 900 proceeds to step 906.

At step 906, bifunctional antibody(ies) 202 associated with small particle(s) 100 detect and bind to one or more FcεRI receptors 304 associated with one or more target cells 302 (not shown in FIG. 9), including mast cells and basophils, as well as any other appropriate cells as may be apparent to those skilled in the relevant art(s) after reading the description herein. In some aspects, each bifunctional antibody 202 may bind to a single FcεRI receptor 304. In some additional aspects, target cell(s) 302 may be associated with one or more actions associated with an allergic reaction. In still some additional aspects, target cell(s) 302 may be in proximity to one or more locations, regions, processes, functions, diseases, disorders, systems, organs, and/or other cells 310 (not shown in FIG. 9) within a human body where one or more actions associated with an allergic reaction/allergy cascade may be occurring. Such aspects allow for targeted treatment of allergic reactions/allergy cascades by guiding small particle(s) 100 to where they are needed, thereby allowing relatively high concentrations and/or quantities of antihistamine(s) 102 to be delivered to an individual, as well as allowing multiple different types and/or forms of antihistamine(s) 102 to be delivered to an individual simultaneously.

In some aspects, target cell(s) 302 may be located within one or more portions of human respiratory system 400 (not shown in FIG. 9), including but not limited to the nasal cavity, trachea 408 (not shown in FIG. 9), one or more bronchi 410 (not shown in FIG. 9), one or both of lungs 412 (not shown in FIG. 9), one or more alveoli (not shown in FIG. 9), one or more alveolar ducts (not shown in FIG. 9), one or more respiratory bronchioles (not shown in FIG. 9), and the like. In some additional aspects, target cell(s) 302 may be accessed via system circulation 416 (not shown in FIG. 9). In such aspects, small particle(s) 100 may enter systemic circulation 416 via intranasal means and/or by being absorbed into systemic circulation 416 through one or more surfaces 414 (not shown in FIG. 9) of one or both lungs 412 or through one or more nasal structures and/or other surfaces associated with human respiratory system 400, by intravenous injection, or via any other appropriate means and/or method as may be apparent to those skilled in the relevant art(s) after reading the description herein.

Once bifunctional antibody(ies) 202 of small particle(s) 100 have bound to target cell(s) 302, process 900 proceeds to step 908.

At step 908, small particle(s) 100 release one or more antihistamines 102 from within them. In some aspects, one or more outer surfaces and/or membranes of small particle(s) 100 may break down and/or otherwise decompose in order to release and/or expose the one or more antihistamines 102. In some additional aspects, small particle(s) 100 may fuse with one or more target cells 302 and/or other cells 310. Upon fusing with such cells, one or more outer surfaces and/or membranes of small particle(s) 100 may open up or otherwise alter in structure and/or composition in order to allow one or more antihistamine(s) 102 to leave small particle(s) 100 enter target cell(s) 302 and/or other cell(s) 310; or, in some aspects, antihistamine(s) 102 may pass through outer surface(s)/membrane(s) of small particle(s) 100 and into target cell(s) 302, other cell(s) 310, or any other appropriate area, region, system, organ, or cell as may be apparent to those skilled in the relevant art(s) after reading the description herein.

Once antihistamine(s) 102 have been released from small particle(s) 100, process 900 proceeds to step 910.

At step 910, antihistamine(s) 102 intervene in one or more actions associated with an allergic reaction. By way of example and not limitation, antihistamine(s) 102 may comprise one or more mast cell stabilizers, basophil stabilizers, $H_1$ antagonists, corticosteroids, leukotriene receptor antagonists, or any combination thereof.

Mast cell stabilizers and basophil stabilizers may function by blocking one or more calcium channels within mast cells and basophils, respectively, that are needed for cell degranulation. If mast cells and/or basophils are not able to go through the degranulation process, then they do not release any histamine molecules 308 (not shown in FIG. 9). $H_1$ antagonists may function by blocking the interaction of histamine molecules 308 with receptors 312 (not shown in FIG. 9) on various other cells 310, including $H_1$ receptors, in order to prevent other cells 310 from expressing the symptoms of and/or experiencing one or more actions associated with an allergic reaction or allergy cascade, such as, by way of example and not limitation, inflammation. By way of example and not limitation, other cells 310 may comprise smooth muscle cells, mucous glands, sensory nerve endings, as well as any other appropriate type of cell as may be apparent to those skilled in the relevant art(s) after reading the description herein. Corticosteroids may function by preventing or minimizing inflammation at different sites within the body, while leukotriene receptor antagonists may function by blocking one or more chemical reactions that may lead to inflammation within the various airways of human respirator)/system 400, including but not limited to the nasal cavity, trachea 408, one or more bronchi 410, one or both of lungs 412, one or more alveoli one or more alveolar ducts, one or more respiratory bronchioles and the like.

Once at least one action associated with an allergic reaction has been presented and/or stopped, process 900 proceeds to step 912

At step 912, process 900 is terminated and process 900 ends.

Figure 10:
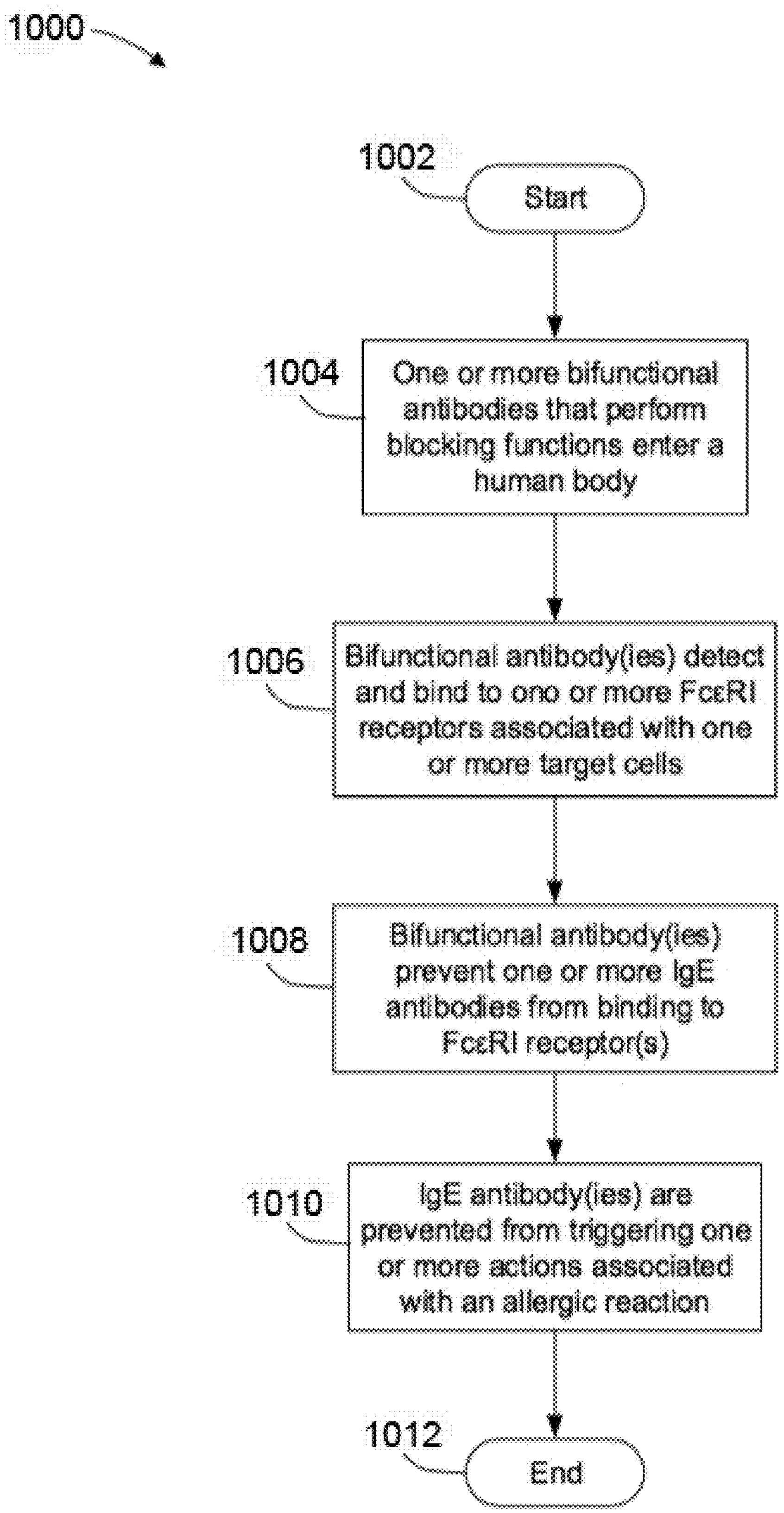
FIG. 10 is a flowchart illustrating an exemplary process for intervening in one or more actions associated with an allergic reaction within a human body using one or more bifunctional antibodies that perform blocking functions, according to an aspect of the present disclosure.

Referring now to FIG. 10, a flowchart illustrating an exemplary process 1000 for intervening in one or more actions associated with an allergic reaction within a human body using one or more bifunctional antibodies 202 (not shown in FIG. 10) that perform blocking functions, according to an aspect of the present disclosure, is shown.

Process 1000 begins at step 1002 with control passing immediately to step 1004.

At step 1004, one or more bifunctional antibody(ies) 202 that perform blocking functions enter a human body. In some aspects, such bifunctional antibody(ies) 202 may be integrated with one or more small particles 100. Small particle(s) 100 may be of the first and/or second variation. As previously discussed, in some aspects, small particle(s) 100 of the first variation may comprise a relatively larger size than small particle(s) 100 of the second variation. In some additional aspects, small particle(s) 100 that enter the human body at step 1004 may comprise one or more antihistamines 102 (not shown in FIG. 10). Bifunctional antibody(ies) 202 may enter the human body via human nose 404 (not shown in FIG. 10), human respiratory system, or intravenously (not shown in FIG. 10), one or more delivery means may be used, as may be apparent to those skilled in the relevant art(s) after reading the description herein.

Once bifunctional antibody(ies) 202 have entered the human body, process 1000 proceeds to step 1006.

At step 1006, bifunctional antibody(ies) 202 detect and bind to one or more FcεRI receptors 304 (not shown in FIG. 10) associated with one or more target cells 302 (not shown in FIG. 10), including mast cells and basophils, as well as any other appropriate cells as may be apparent to those skilled in the relevant art(s) after reading the description herein. In some aspects, each bifunctional antibody 202 may bind to a single FcεRI receptor 304. In some additional aspects, target cell(s) 302 may be associated with one or more actions associated with an allergic reaction. In some additional aspects, target cell(s) 302 may be in proximity to one or more locations, regions, processes, functions, diseases, disorders, systems, organs, and/or other cells 310 (not shown in FIG. 10) within a human body where one or more actions associated with an allergic reaction may be occurring.

In some aspects, target cell(s) 302 may be located within one or more portions of human respiratory system 400, including but not limited to the nasal cavity, trachea 408 (not shown in FIG. 10), one or more bronchi 410 (not shown in FIG. 10), one or both of lungs 412 (not shown in FIG. 10), one or more alveoli (not shown in FIG. 10), one or more alveolar ducts (not shown in FIG. 10), one or more respiratory bronchioles (not shown in FIG. 10), and the like. In some additional aspects, target cell(s) 302 may be accessed via system circulation 416 (not shown in FIG. 10). In such aspects, bifunctional antibody(ies) 202 may enter systemic circulation 416 via intranasal means and/or by being absorbed into systemic circulation 416 through one or more surfaces 414 (not shown in FIG. 10) of one or both lungs 412 or through one or more nasal structures and/or other surfaces associated with human respiratory system 400, by intravenous injection, or via any other appropriate means and/or method as may be apparent to those skilled in the relevant art(s) after reading the description herein.

Once bifunctional antibody(ies) 202 have bound to target cell(s) 302, process 1000 proceeds to step 1008.

At step 1008, bifunctional antibody(ies) 202 prevent one or more IgE antibodies from binding to FcεRI receptor(s) 304. In some aspects, IgE antibodies cannot bind to FcεRI receptor(s) 304 to which one or more bifunctional antibody(ies) 202 are already bound. Process 1000 then proceeds to step 1010.

At step 1010, the IgE antibodies that cannot bind to FcεRI receptor(s) 304 are prevented from triggering one or more actions associated with an allergic reaction. In some aspects, if IgE antibodies, which may or may not be specific to various allergens, are not able to bind to FcεRI receptor(s) 304, they cannot undergo the process of cross-linking 306 and no aggregation of FcεRI receptor(s) 304 occurs upon the surface(s) of target cell(s) 302, thereby preventing the triggering of any degranulation processes that target cell(s) 302 would otherwise undergo if those events were able to take place. Target cell(s) 302 that do not go through degranulation do not release any histamine molecules 308 (not shown in FIG. 10) and therefore no allergic reaction or allergy cascade takes place. Process 1000 then proceeds to step 1012.

At step 1012, process 1000 is terminated and process 1000 ends.

Figure 11:
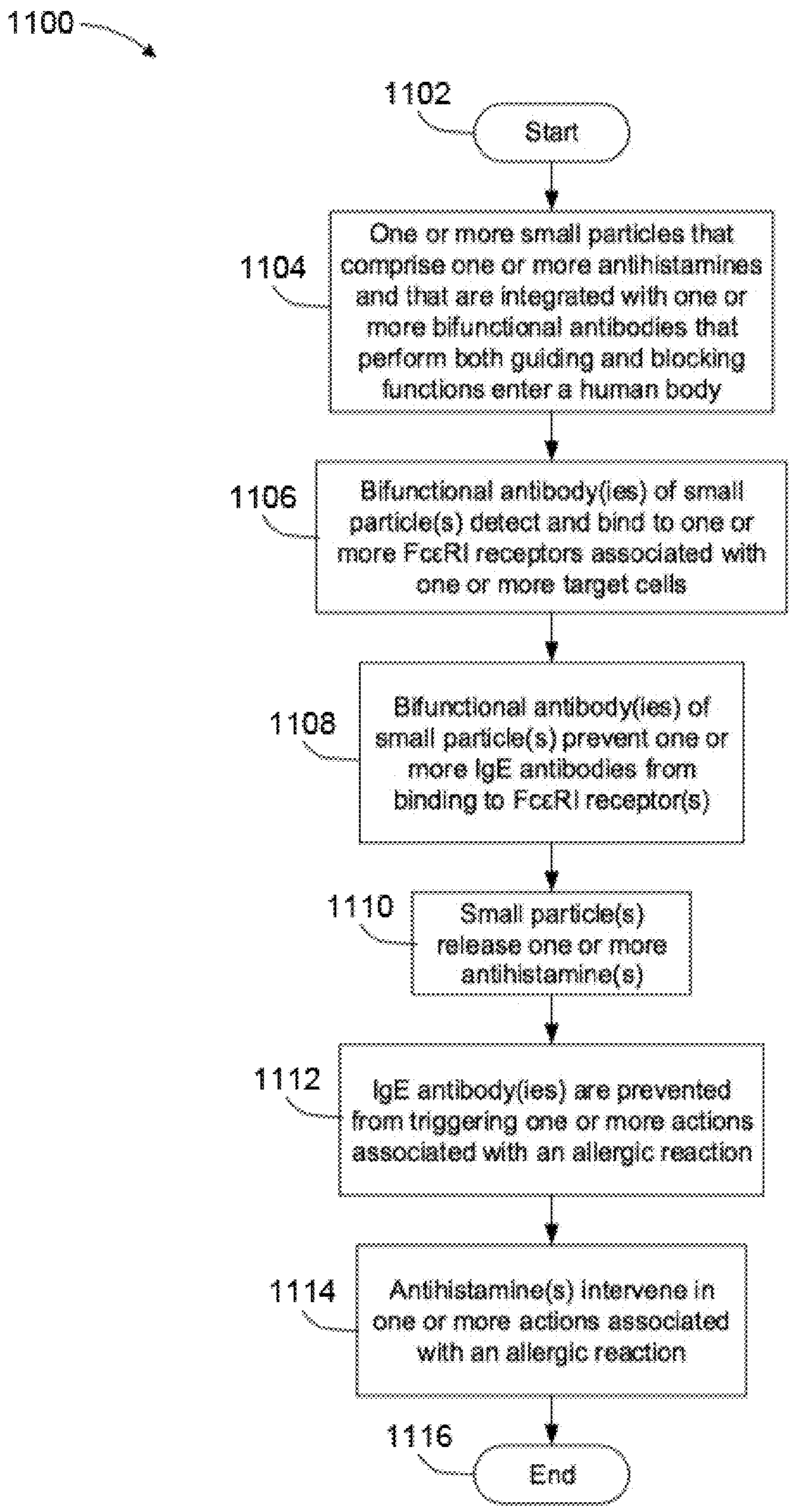
FIG. 11 is a flowchart illustrating an exemplary process for intervening in one or more actions associated with an allergic reaction within a human body using one or small particles comprising one or more antihistamines, wherein the one or more small particles are integrated with one or more bifunctional antibodies that perform both guiding and blocking functions, according to an aspect of the present disclosure.

Referring now to FIG. 11, a flowchart illustrating an exemplary process 1100 for intervening in one or more actions associated with an allergic reaction within a human body using one or small particles 100 (not shown in FIG. 11) comprising one or more antihistamines 102 (not shown in FIG. 11), wherein the one or more small particles 100 are integrated with one or more bifunctional antibodies 202 (not shown in FIG. 11) that perform both guiding and blocking functions, according to an aspect of the present disclosure, is shown.

Process 1100 begins at step 1102 with control passing immediately to step 1104.

At step 1104, one or more small particles 100 that are integrated with one or more bifunctional antibodies 202 that perform both guiding and blocking functions enter a human body. Small particle(s) 100 may be of the first and/or second variation. As previously discussed, in some aspects, small particle(s) 100 of the first variation may comprise a relatively larger size than small particle(s) 100 of the second variation. In some additional aspects, small particle(s) 100 that enter the human body at step 1104 may comprise one or more antihistamines 102. Small particles(s) 100 may enter the human body via human nose 404 (not shown in FIG. 11), human respiratory tract, or intravenously, as well as any other appropriate delivery devices/means as may be apparent to those skilled in the relevant art(s) after reading the description herein.

Once small particle(s) 100 have entered the human body, process 1100 proceeds to step 1106.

At step 1106, bifunctional antibody(ies) 202 associated with small particle(s) 100 detect and bind to one or more FcεRI receptors 304 (not shown in FIG. 11) associated with one or more target cells 302 (not shown in FIG. 11), including mast cells and basophils, as well as any other appropriate cells as may be apparent to those skilled in the relevant art(s) after reading the description herein. In some aspects, each bifunctional antibody 202 may bind to a single FcεRI receptor 304. In some additional aspects, target cell(s) 302 may be associated with one or more actions associated with an allergic reaction. In still some additional aspects, target cell(s) 302 may be in proximity to one or more locations, regions, processes, functions, diseases, disorders, systems, organs, and/or other cells 310 (not shown in FIG. 11) within a human body where one or more actions associated with an allergic reaction may be occurring. Such aspects may allow for targeted treatment of allergic reactions/allergy cascades by guiding small particle(s) 100 to where they are needed, thereby allowing relatively high concentrations and/or quantities of antihistamine(s) 102 to be delivered to an individual, as well as allowing multiple different types and/or forms of antihistamine(s) 102 to be delivered to an individual simultaneously.

In some aspects, target cell(s) 302 may be located within one or more portions of human respiratory system 400 (not shown in FIG. 11), including but not limited to the nasal cavity, trachea 408 (not shown in FIG. 11), one or more bronchi 410 (not shown in FIG. 11), one or both of lungs 412 (not shown in FIG. 11), one or more alveoli (not shown in FIG. 11), one or more alveolar ducts (not shown in FIG. 11), one or more respiratory bronchioles (not shown in FIG. 11), and the like. In some additional aspects, target cell(s) 302 may be accessed via system circulation 416 (not shown in FIG. 11). In such aspects, small particle(s) 100 may enter systemic circulation 416 via intranasal means and/or by being absorbed into systemic circulation 416 through one or more surfaces 414 (not shown in FIG. 11) of one or both lungs 412 or through one or more nasal structures and/or other surfaces associated with human respiratory system 400, or intravenously or via any other appropriate means and/or method as may be apparent to those skilled in the relevant art(s) after reading the description herein.

Once bifunctional antibody(ies) 202 of small particle(s) 100 have bound to target cell(s) 302, process 1100 proceeds to step 1108.

At step 1108, bifunctional antibody(ies) 202 associated with small particle(s) 100 prevent one or more IgE antibodies from binding to FcεRI receptor(s) 304. In some aspects, IgE antibodies cannot bind to FcεRI receptor(s) 304 to which one or more bifunctional antibodies 202 are already bound. Process 1100 then proceeds to step 1110.

At step 1110, small particle(s) 100 release one or more antihistamines 102 from within them. In some aspects, one or more outer surfaces and/or membranes of small particle(s) 100 may break down and/or otherwise decompose in order to release the one or more antihistamines 102. In some additional aspects, small particle(s) 100 may fuse with one or more target cells 302 and/or other cells 310. Upon fusing with such cells, one or more outer surfaces and/or membranes of small particle(s) 100 may open up or otherwise alter in structure and/or composition in order to allow one or more antihistamine(s) 102 to leave small particle(s) 100 and enter target cell(s) 302 and/or other cell(s) 310; or, in some aspects, antihistamine(s) 102 may pass through outer surface(s)/membrane(s) of small particle(s) 100 and into target cell(s) 302, other cell(s) 310, or any other appropriate area, region, system, organ, or cell as may be apparent to those skilled in the relevant art(s) after reading the description herein.

Once antihistamine(s) 102 have been released from small particle(s) 100, process 1100 proceeds to step 1112.

At step 1112, the IgE antibodies that cannot bind to FcεRI receptor(s) 304 are prevented from triggering one or more actions associated with an allergic reaction. In some aspects, if IgE antibodies, which may or may not be specific to various allergens, are not able to bind to FcεRI receptor(s) 304, they cannot undergo the process of cross-linking 306 and no aggregation of FcεRI receptor(s) 304 occurs upon the surface(s) of target cell(s) 302, thereby preventing the triggering of any degranulation processes that target cell(s) 302 would otherwise undergo if those events had taken place. Target cell(s) 302 that do not go through degranulation do not release any histamine molecules 308 (not shown in FIG. 11) and therefore no allergic reaction or allergy cascade takes place. Process 1100 then proceeds to step 1114.

At step 1114, antihistamine(s) 102 intervene in one or more actions associated with an allergic reaction. By way of example and not limitation, antihistamine(s) 102 may comprise one or more mast cell stabilizers, basophil stabilizers, $H_1$ antagonists, corticosteroids, leukotriene receptor antagonists, or any combination thereof.

Mast cell stabilizers and basophil stabilizers may function by blocking one or more calcium channels within mast cells and basophils, respectively, that are needed for cell degranulation if mast cells and/or basophils are not able to go through the degranulation process, then they do not release any histamine molecules 308. $H_1$, antagonists may function by blocking the interaction of histamine molecules 308 with receptors 312 (not shown in FIG. 11) on various other cells 310, including $H_1$ receptors, in order to prevent other cells 310 from expressing the symptoms of and/or experiencing one or more actions associated with an allergic reaction or allergy cascade, such as, by way of example and not limitation, inflammation. By way of example and not limitation, other cells 310 may comprise smooth muscle cells, mucous glands, sensory nerve endings, as well as any other appropriate type of cell as may be apparent to those skilled in the relevant art(s) after reading the description herein. Corticosteroids may function by preventing or minimizing inflammation at different sites within the body, while leukotriene receptor antagonists may function by blocking one or more chemical reactions that may lead to inflammation within the various airways of human respiratory system 400, including but not limited to the nasal cavity, trachea 408, one or more bronchi 410, one or both of lungs 412, one Or more alveoli, one or more alveolar ducts, one or more respiratory bronchioles, and the like.

Once at least one action associated with an allergic reaction has been prevented and/or stopped, process 1100 proceeds to step 1116.

At step 1116 process 1100 is terminated and process 1100 ends.

As will be apparent to those skilled in the relevant art(s) after reading the description herein, steps 1108, 1110, 1112, and 1114 may occur at substantially similar times. In some aspects, steps 1108-1114 may occur substantially simultaneously. In some additional aspects, steps 1108-1114 may occur within a few seconds, minutes, or hours of each other. In still some additional aspects, steps 1108-1114 may occur in various orders, such as, by way of example and not limitation, step 1110 occurring first, followed by step 1108, followed by step 1114, and finally, followed by step 1112. Other orders may be possible as well and shall not be limited to any specific order exemplified in the present disclosure.

Regarding the effect of control on the dose, in order to achieve a concentration that is effective, when one takes an antihistamine, the concentrations achieved in the whole body will broadly start as equal. That would require the drug to be taken in accord with the whole body volume, most of which is "wasted" in parts of the body where the allergy reaction is not taking place. Indeed, it is this "wasted" high concentration of drug that gives many adverse events. By having means to target only the offending cells using guiding antibody, as disclosed herein, local release in the vicinity of the reaction is achieved, and then high concentrations are needed to be released only at or near the reaction site.

A second effect of control on the dose is that the liposome with PEG slows down the release and degradation of the antihistamines. The body is constantly metabolizing pharmaceuticals. Thus, to maintain certain concentrations that are required for antihistamine effect, patients need to take the available pills frequently or deliver high doses each time so that the effect lasts. On the other hand, the PEG-liposome is stable, stays in circulation longer (actually stays around mast cells and basophils longer), and releases the antihistamines at a controlled rate and thus counteracting the effect of rapid metabolism; and that controlled to within vicinity of where they are required to act. Patients thus take the treatment less frequently.

In an embodiment, the bifunctional antibody itself blocks crosslinking and release of histamine, so that there is less histamine to block, lowering the amounts of antihistamines required.

The following are some of the properties contemplated for an embodiment: (1) an inhalational product that is administered once a day, or even once a week; (2) an inhalation agent that starts to work within 10-15 minutes, instead of hours; (3) use of 10-fold lower antihistamine concentrations/doses than current technologies; (4) use of multiple antihistamines at the same time without the side effects.

Reference will now be made to specific examples illustrating the disclosure. It is to be understood that the examples are provided to illustrate exemplary embodiments and that no limitation to the scope of the disclosure is intended thereby.

EXAMPLES

Example 1: Synthesis of Proprietary Antibodies

We have generated guiding and blocking monoclonal antibodies for the human FcεR. We generated monoclonal antibodies (mAb) to human FcεRI by injecting FcεRI into mice, selecting the cells, and producing these antibodies, and then by fusing them to multiple myeloma cells to produce hybridomas. Thus, we have proprietary hybridoma cell lines which are used to generate various embodiments disclosed here. The binding characteristics of the antibodies, and their specificity against human FcεRI were examined, first in a screening assay, and then as full kinetic data.

Project Development

One goal of the project was to develop monoclonal antibodies (mAbs) against the human FcεRI α-protein, for use as guiding and functional blocking mAbs that do not cross-link when bound to target, to be used in patients with various allergic reactions. One goal was to generate such antibodies, determine their affinity for the target, and determine their specificity (degree or lack of binding to animal receptors and non-FcεRI human proteins).

Materials & Animals

The total amount of antigen was ling of recombinant human FcεRI α-protein (21.9 kDa), supplied by R&D Systems (Cat #6678-Fc-050). We also used an adjuvant. In addition, we utilized five Swiss Jim Lambert (SJL) mice.

Immunization

Precision Antibody Proprietary Technology was used for immunizations on five SJL/J mice. Immunizations were initiated, and then the first tail bleed was obtained after about two weeks. After the tail bleed, titers were examined using the recombinant human FcεRI α-protein (Ag1) at 100 ng/well in PBS in MB plate, with 3% Milk-PBS as a negative control, in competitive EIA assays. Results are shown in Table 1.

TABLE I

| Dilution | Mouse#1 | Mouse#2 | Mouse#3 | Mouse#4 | Mouse#5 |
|---|---|---|---|---|---|
| 1:1,000 | 0.092 | 0.068 | 0.068 | 0.112 | 0.107 |
| 1:3,000 | 0.073 | 0.060 | 0.059 | 0.068 | 0.079 |
| 1:10,000 | 0.054 | 0.050 | 0.059 | 0.058 | 0.063 |
| 1:30,000 | 0.050 | 0.048 | 0.047 | 0.049 | 0.049 |
| 1:100,000 | 0.049 | 0.047 | 0.047 | 0.047 | 0.047 |
| Negative Control | 0.048 | 0.047 | 0.047 | 0.050 | 0.051 |

The titers shown were weak, therefore additional boosts were made to increase the titers and a second tail bleed was conducted five days after the first tail bleed. The target antigen was coated at 200 ng/well on both medium binding plate and high binding plate, with results shown in Table 2. Mouse #1 and mouse ∩3 died, and the results are shown for the three remaining mice.

TABLE 2

| Dilution | OD1 (MB) | OD2 (HB) |
|---|---|---|
| Mouse#2 (1:1,000) | 1.061 | OVRFLW |
| Mouse#2 (1:3,000) | 0.360 | OVRFLW |
| Mouse#2 (1:10,000) | 0.324 | 3.907 |
| Mouse#2 (1:30,000) | 0.139 | 2.144 |
| Mouse#2 (1:100,000) | 0.071 | 0.691 |
| Negative Control | 0.042 | 0.114 |
| TB1 M#2 @1:1000 | 0.791 | OVRFILW |
| Mouse#4 (1:1,000) | 2.116 | OVRFLW |
| Mouse#4 (1:3,000) | 1.014 | OVRELW |
| Mouse#4 (1:10,000) | 1.043 | OVRFLW |
| Mouse#4 (1:30,000) | 0.649 | OVRFLW |
| Mouse#4 (1:100,000) | 0.309 | 2.732 |
| Negative Control | 0.042 | 0.045 |
| TB1 M#4 @1:1000 | 0.716 | OVRFLW |
| Mouse#5 (1:1,000) | 1.228 | OVRFLW |
| Mouse#5 (1:3,000) | 0.621 | OVRFLW |
| Mouse#5 (1:10,000) | 0.593 | 3.886 |
| Mouse#5 (1:30,000) | 0.101 | 2.850 |
| Mouse#5 (1:100,000) | 0.088 | 1.385 |
| Negative Control | 0.043 | 0.050 |
| TB1 M#5 @1:1000 | 0.814 | OVRFLW |

Table 2 shows that the titers were very strong for high binding plate. Therefore, we chose mouse #4 and mouse #5 for final boosts, and fusion.

Fusion, Cloning, and Screening

We performed single fusion of splenocytes and lymph nodes of mice #4 and mouse #5. Fusion was completed 2-3 weeks after the second tail bleed. A portion of the fusion was cloned and screened for specificity to the target antigen. The remaining fused polyclonal material was frozen and stored. Monoclonal antibody initial screening was performed via an ELISA primary screen, with target protein as the human FcεRI α-protein. Those chosen for primary screening were then expanded in order to generate antibodies for a final confirmatory ELISA assay. Seven positive clones were confirmed in an assay of the recombinant FcεRI α-protein at 100 ng/well in PBS in HB plate. Results are as shown in Table 3; negative controls were 3% Milk/PBS and Positive Controls were Cardiac Serum (1:1,000) dilution in 3% Milk/PBS.

TABLE 3

| Well Number | Concentration |
|---|---|
| 1C1 | 2.922 |
| 1C3 | 3.143 |

TABLE 3-continued

| Well Number | Concentration |
|---|---|
| 5H10 | 3.187 |
| 6G9 | 3.139 |
| 6H9 | 3.039 |
| 8H6 | 3.555 |
| 9A11 | 3.007 |
| NC | 0.039 |
| PC | 3.454 |

5-9 ml of culture supernatant from Clones: 1C1, 1C3, 5H10, 6G9, 6H9, 8H6, 9A11, which demonstrated specificity, as well as 1 control medium, were prepared, and frozen. Clones 1C1, 1C3, 5H10, 6G9, 6H9, 8H6, 9A11 have also been stored and archived for future production of monoclonal antibodies.

Antibody Production

Up to 5×0.5-5 mg Production w/Purification, Isotyping of Clone, & Buffer Exchange to PBS (conc. ~1 mg/ml) is produced from the hybridomas for further development of antibody and extra tests that will be run. We utilize a hollow fiber/bioreactor system for harvesting large amounts of antibody.

Example 2: Characterization of FcεR-Binding Monoclonal Antibodies

For scouting and for obtaining full kinetics parameters for the antibodies, we used Octet Technology, in particular Octet® RED96.

Octet Technology

The Octet® RED96 is an instrument that can provide information similar to that provided by Biacore (SPR), but by using a different technology. The technology is called Bio-Layer Interferometry (BLI), which is label-free and can be used for measuring bio-molecular interactions such as protein:protein binding, quantitation, affinity, and kinetics. ForteBio, the manufacturer of the instrument, provides additional descriptions on its website at http://www.fortebio.com/bli_technology.html.

The Assay: Scouting Affinity for Ranking

For loading, the murine mAb's from the culture supernatants were captured using Anti-mouse IgG Fc Capture (AMC) dip and biosensors. For association, sensors were dipped into Ag (as indicated) at a series of concentrations starting from 1000 nM to lower with 2 fold serial dilution in 1× kinetic buffer (PBS, 0.01% BSA, 0.002% tween 20) as indicated (e.g., in the brief description of the relevant drawings) for full kinetics. For dissociation, the probes were dipped into assay buffer (1× kinetic buffer) and the dissociation rate (off rate) was measured. For analysis, a 1:1 curve fitting analysis was performed to determine $k_{on}$, $k_{off}$, $K_D$. The graphs display the binding response by a nanometer shift in the BLI platform vs. the time (seconds).

Results

Figure 12A:
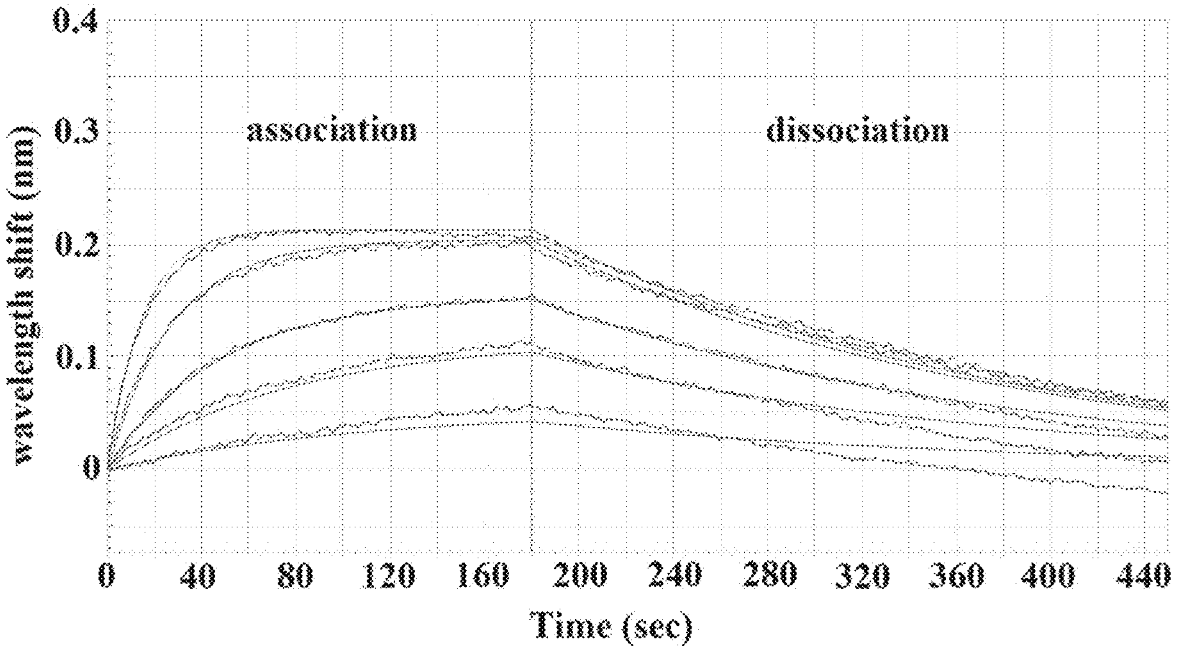
FIGS. 12A-12E depict the binding response by a nanometer wavelength shift in the Bio-Layer Interferometry (BLI) platform vs. time. In each case, Hu. Fc epsilon RI alpha protein is used in five different concentrations, 62.5 nM, 125 nM, 250 nM, 500 nM, and 1000 nM, data for each being shown in non-smooth lines. The smooth lines are the model estimates of the vendor.
Figure 12B:
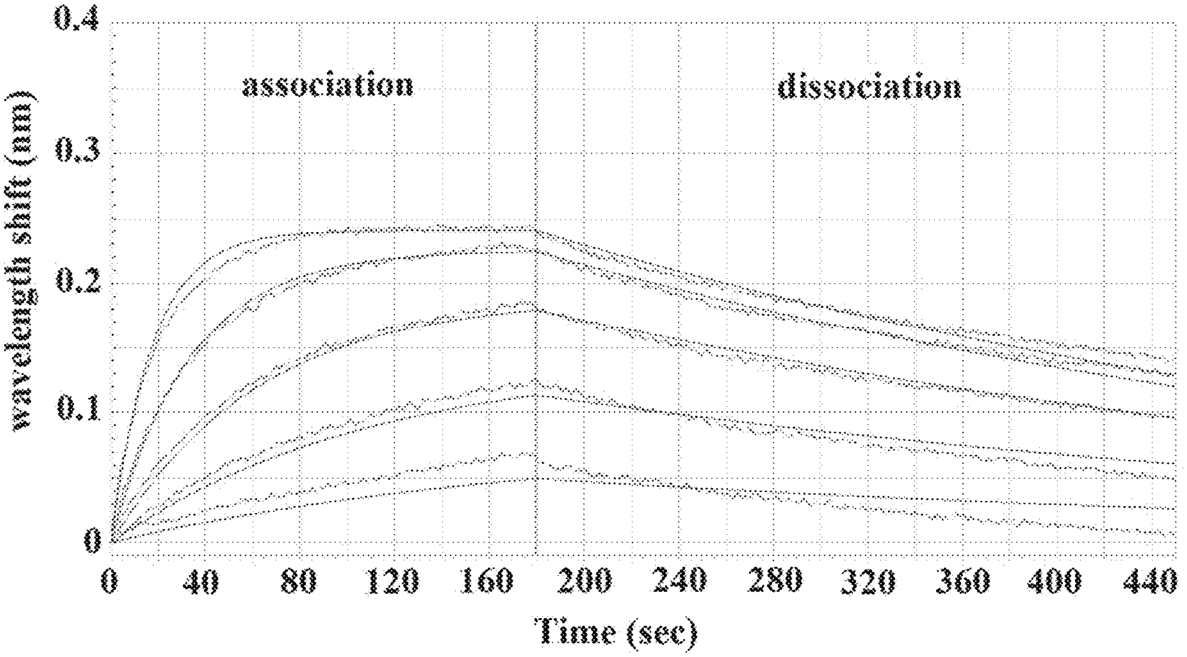
Figure 12C:
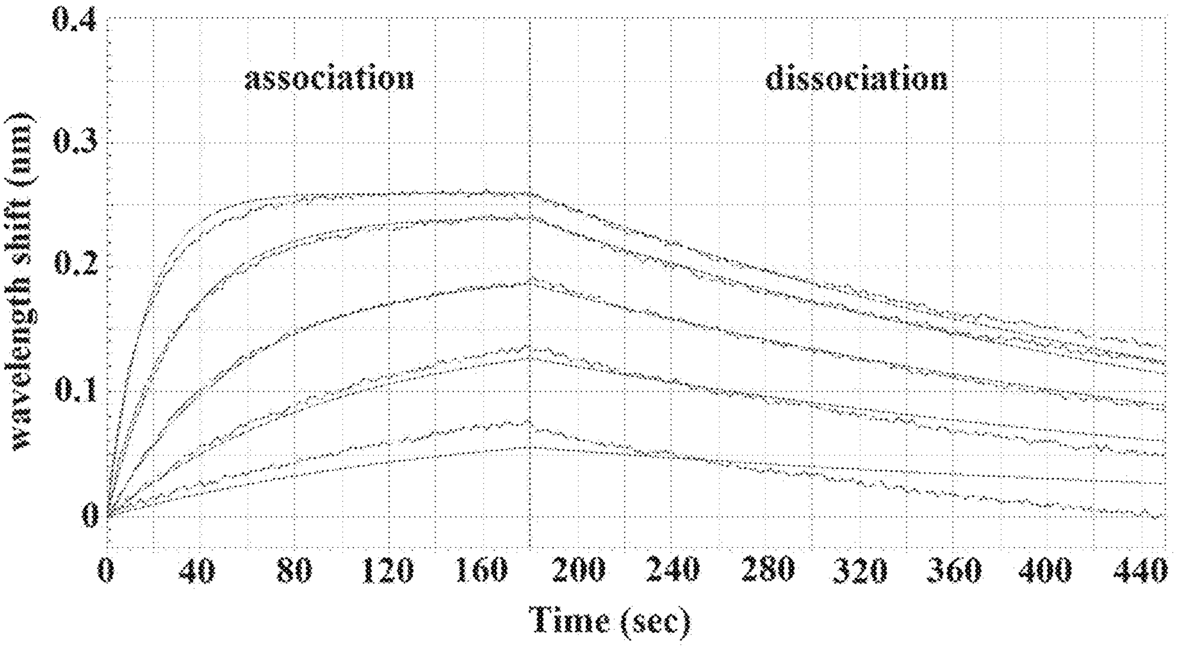
Figure 12D:
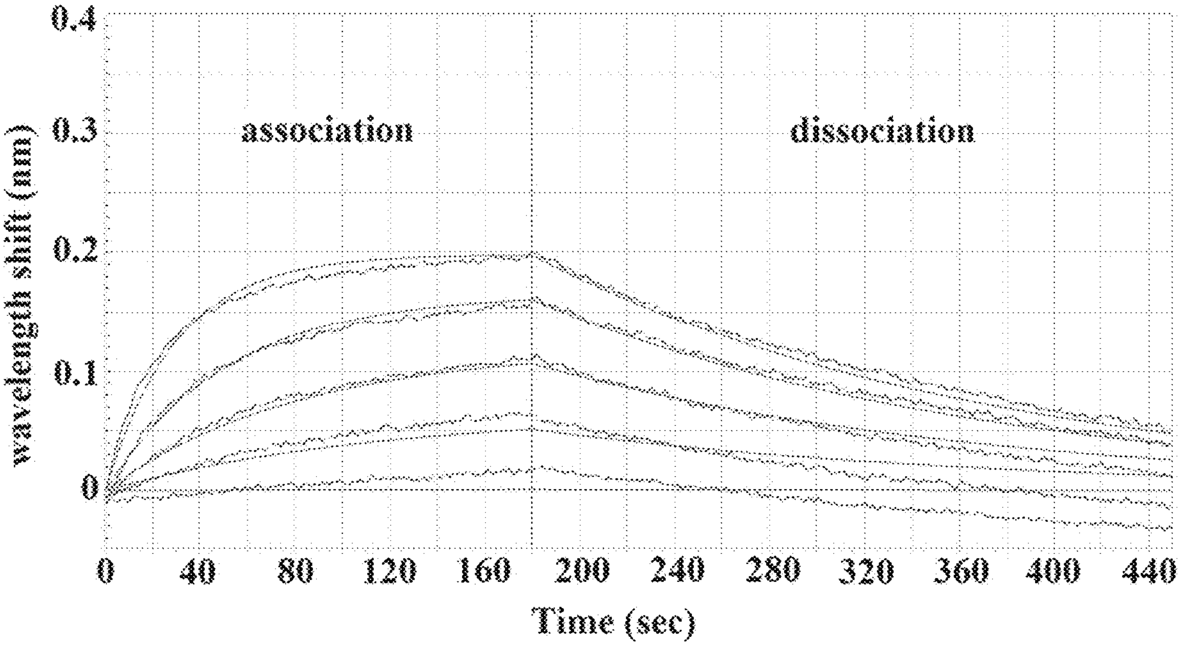
Figure 12E:
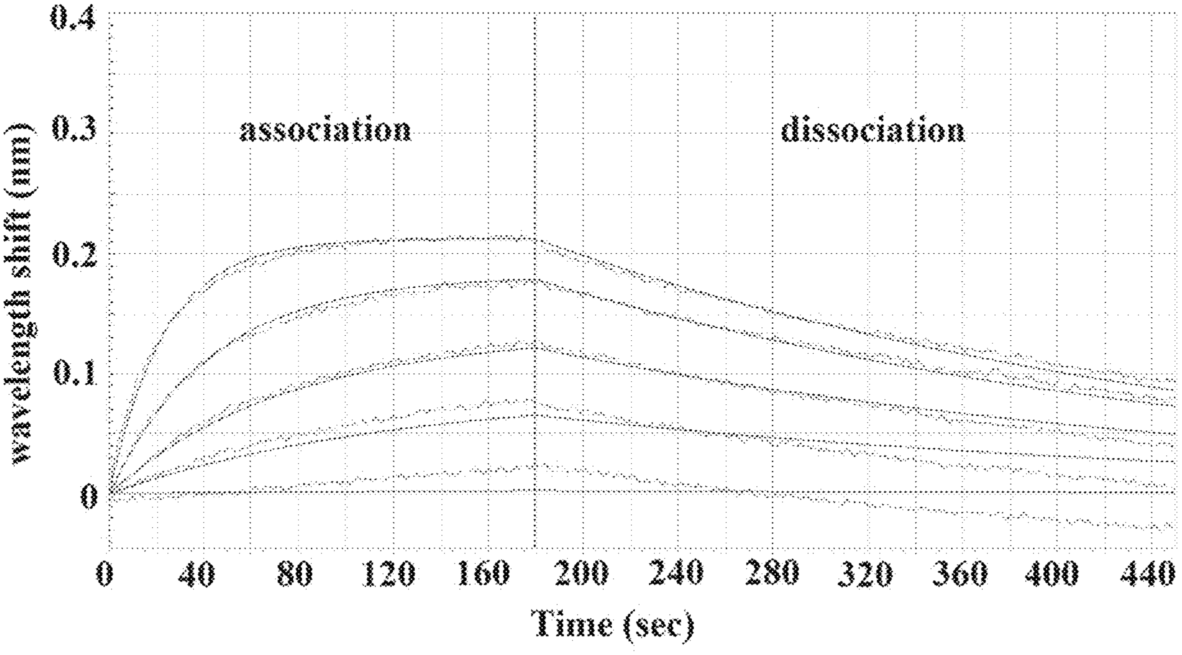

A typical scouting affinity kinetics run had the following steps: (1) BPP (Biosensor probe preparation); (2) Capture of mAb at 20 ug/ml in assay buffer—mAbs bind to the anti-mouse coated probes; (3) Baseline in assay buffer (1× kinetic buffer or PBS); (4) Association with Ag; (5) Dissociation—assay buffer. For parallel reference subtraction, Ag binding response on pooled purified ms IgG was loaded to AMC sensor at an equal amount as test Ab was taken. The full kinetics curves for 1C1 are shown in FIG. 12A; for 8H6 in FIG. 12B; for 6G9 in FIG. 12C; for 6H9 in FIG. 12D; and for 5H10 in FIG. 12E.

TABLE 4

| Loading Sample ID | Sample ID | Conc. (nM) | kdis(1/s) | kon(1/Ms) | KD (M) | Full X^2 | Full R^2 |
|---|---|---|---|---|---|---|---|
| ICI | Hu Fc epsilon RI alpha protein | 1000-0 | $5.03 \times 10^{-3}$ | $6.23 \times 10^4$ | $8.15 \times 10^{-8}$ | 0.20939 | 0.9787 |
| 8H6 | Hu Fc epsilon RI alpha protein | 1000-0 | $2.32 \times 10^{-3}$ | $5.50 \times 10^4$ | $4.21 \times 10^{-8}$ | 0.151 | 0.986 |
| 6G9 | HuFc epsilon RI alpha protein | 1000-0 | $2.75 \times 10^{-3}$ | $5.78 \times 10^4$ | $4.75 \times 10^{-8}$ | 0.1715 | 0.986 |
| 6H9 | Hu Fc epsilon RI alpha protein | 1000-0 | $5.26 \times 10^{-3}$ | $2.80 \times 10^4$ | $1.88 \times 10^{-7}$ | 0.266 | 0.968 |
| 5H10 | Hu Fc epsilon RI alpha protein | 1000-0 | $3.35 \times 10^{-3}$ | $3.93 \times 10^4$ | $8.53 \times 10^{-8}$ | 0.2193 | 0.9782 |

CONCLUSIONS

Based on the observations, we may conclude that all the 5 mAbs tested have very similar affinities, however we could place them from highest to lowest affinities in the following order: 8H6>6G9>1C1>5H10>6H9.

The antibodies we have generated and produced have a sufficiently strong binding affinity for human FcεR. Natural human IgE has the following $k_D$ (dissociation constant) values: $10^{-10}$ M for FcεRI (high affinity receptor) and $10^{-7}$ M for FcεRII (low affinity receptor). We utilized Octet Technology, which produces the same information as the standard Biacore (SPR), to identify the $K_D$ of our mAb ti human FcεR a protein. Four of these had the following $K_D$ values: $4.21 \times 10^{-8}$ M, $4.75 \times 10^{-8}$ M, $8.15 \times 10^{-8}$ M and $8.53 \times 10^3$ M. Moreover, the $k_{off}$ ($k_{dis}$) rates of $2\text{-}5 \times 10^{-3}$ per second are in the range for human IgE and FcεR ($6 \times 10^{-3}\text{-}3.8 \times 10_{-4}$ per second), which means that once bound, the mAb (and its cargo) will have a long half-life of several days as well. This affinity, which is intermediate between high and low affinity values for the FcεR, is sufficient for the function of (a) guiding antibody, and (b) blocking antibody function, since the mechanism of effect of the invention is not competitive inhibition of IgE, but rather the two step process of (a) binding without producing cross linking, and (h) release of antihistamines.

While various aspects of the present disclosure have been described above, it should be understood that they have been presented by way of example and not limitation. It will be apparent to persons skilled in the relevant art(s) that various changes in form and detail can be made therein without departing from the spirit and scope of the present disclosure. Thus, the present disclosure should not be limited by any of the above described exemplary aspects, but should be defined only in accordance with the following claims and their equivalents.

In addition, it should be understood that the figures in the attachments, which highlight the structure, methodology, functionality, and advantages of the present disclosure, are presented for example purposes only. The present disclosure may be implemented in ways other than that shown in the accompanying figures (e.g., implementation within delivery devices and configurations other than those mentioned herein). As will be appreciated by those skilled in the relevant art(s) after reading the description herein, certain features from different aspects of the methods and small particles of the present disclosure may be combined to form yet new aspects of the present disclosure.

Further, the purpose of the foregoing Abstract is to enable the U.S. Patent and Trademark Office and the public generally and especially the scientists, engineers and practitioners in the relevant art(s) who are not familiar with patent or legal terms or phraseology, to determine quickly from a cursory inspection the nature and essence of this technical disclosure. The Abstract is not intended to be limiting as to the scope of the present disclosure in any way.

What is claimed is:

1. A composition comprising:

a nanoparticle comprising an antihistamine and an FcεRI targeting moiety extending from an external surface of the nanoparticle, the targeting moiety comprising an anti-FcεRI antibody or antigen binding fragment thereof, wherein the FcεRI targeting moiety binds the FcεRI on a target cell and blocks target cell degranulation mediated by FcεRI receptor aggregation on the target cell surface, and wherein the antibody or antigen binding fragment thereof comprises a heavy chain having;

a first complementary determining region (CDRH1) comprising SEQ ID NO:3;

a second complementary determining region (CDRH2) comprising SEQ ID NO:4; and a third complementary determining region (CDRH3) comprising SEQ ID NO:5; and a light chain having:

a first complementary determining region CDRL1 comprising SEQ ID NO:8;

a second complementary determining region (CDRL2) comprising SEQ ID NO:9; and a third complementary determining region (CDRL3) comprising SEQ ID NO:10.

2. The composition of claim 1, wherein the antihistamine is selected from the group consisting of azelastine, carbinoxamine, cyproheptadine, desloratadine, emedastine, hydroxyzine, levocabastine, brompheniramine, cetirizine, chlorpheniramine, clemastine, diphenhydramine, fexofenadine, loratadine, and combinations thereof.

3. The composition of claim 1, wherein the nanoparticle is a liposome.

4. The composition of claim 1, wherein the targeting moiety is a monoclonal antibody with a dissociation constant of $4.21\times10^{-8}$ molar.

5. The composition of claim 1, wherein the targeting moiety is a monoclonal antibody that has a dissociation constant that is between $10^{-10}$ molar and $10^{-7}$ molar.

6. The composition of claim 1, wherein the light chain is a kappa light chain.

7. A formulation comprising the composition of claim 1 formulated for low-dose delivery of antihistamine.

8. The formulation of claim 7, wherein the antihistamine is selected from the group consisting of azelastine, carbinoxamine, cyproheptadine, desloratadine, emedastine, hydroxyzine, levocabastine, brompheniramine, cetirizine, chlorpheniramine, clemastine, diphenhydramine, fexofenadine, loratadine, and combinations thereof.

9. The formulation of claim 7, wherein the nanoparticle is a liposome.

10. The formulation of claim 9, wherein at least one type of antihistamine is in an aqueous core of the liposome and at least a second type of antihistamine is in a lipid bilayer of the liposome.

11. The formulation of claim 7, wherein the nanoparticle of the composition is configured for an extended release.

12. The formulation of claim 7 formulated for aerosol delivery.

13. A method for treating an allergic reaction comprising:

obtaining a composition comprising a nanoparticle comprising an antihistamine and an FcεRI targeting moiety extending from an external surface of the nanoparticle, the targeting moiety comprising an anti-FcεRI antibody or antigen binding fragment thereof, wherein the FcεRI targeting moiety binds the FcεRI on a target cell and blocks target cell degranulation mediated by FcεRI receptor aggregation on the target cell surface, and wherein the antibody or antigen binding fragment thereof comprises a heavy chain having;

a first complementary determining region (CDRH1) comprising SEQ ID NO:3;

a second complementary determining region (CDRH2) comprising SEQ ID NO:4; and a third complementary determining region (CDRH3) comprising SEQ ID NO:5; and a light chain having:

a first complementary determining region (CDRL1) comprising SEQ ID NO:8;

a second complementary determining region (CDRL2) comprising SEQ ID NO:9; and a third complementary determining region (CDRL3) comprising SEQ ID NO:10;

and providing the composition to a patient.

14. The method of claim 13 further comprising delivering the antihistamine to a histamine receptor in the patient.

15. The method of claim 13, wherein the composition comprises a second type of antihistamine in the nanoparticle.

16. The method of claim 13, wherein the targeting moiety is a monoclonal antibody, the method further comprising binding of the monoclonal antibody to the FcεR to prevent or minimize cross-linking of IgE and release of mediators.

17. The method of claim 13, wherein the antihistamine is selected from the group consisting of azelastine, carbinoxamine, cyproheptadine, desloratadine, emedastine, hydroxyzine, levocabastine, levocabastine, brompheniramine, cetirizine, chlorpheniramine, clemastine, diphenhydramine, fexofenadine, loratadine, and combinations thereof.

18. The method of claim 13, wherein the nanoparticle is a liposome.

19. The method of claim 13, wherein the FcεR is on a target cell selected from the group consisting of a mast cell, a basophil, and a dendritic cell.

20. The method of claim 13 formulated for low-dose delivery of antihistamine.

21. The method of claim 20 further comprising administering the formulation to the patient.

22. The method of claim 21 further comprising delivering the antihistamine to a histamine receptor in the patient.

23. The method of claim 21 further comprising administering the formulation to the patient a second time after at least two days.

24. The method of claim 21, wherein the at least one antihistamine is selected from the group consisting of azelastine, carbinoxamine, cyproheptadine, desloratadine, emedastine, hydroxyzine, levocabastine, levocabastine, brompheniramine, cetirizine, chlorpheniramine, clemastine, diphenhydramine, fexofenadine, loratadine, and combinations thereof.

25. The method of claim 21, wherein the nanoparticle is a liposome.

26. The method of claim 21 further comprising binding of the antibody to an FcεRI on a target cell to prevent or minimize cross-linking of IgE and release of mediators.

27. The method of claim 26, wherein the target cell is selected from the group consisting of a mast cell, a basophil, and a dendritic cell.

28. The method of claim 21 further comprising delivery of the formulation to portions of a respiratory system of the patient.

* * * * *